United States Patent
Yi et al.

(10) Patent No.: US 12,275,781 B2
(45) Date of Patent: Apr. 15, 2025

(54) MONOCLONAL ANTIBODIES AGAINST MHC-BOUND HUMAN DICKKOPF-1 PEPTIDES AND USES THEREOF

(71) Applicant: Board of Regents, The University of Texas System, Austin, TX (US)

(72) Inventors: Qing Yi, Houston, TX (US); Jianfei Qian, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 819 days.

(21) Appl. No.: 17/425,564

(22) PCT Filed: Feb. 3, 2020

(86) PCT No.: PCT/US2020/016364
§ 371 (c)(1),
(2) Date: Jul. 23, 2021

(87) PCT Pub. No.: WO2020/160532
PCT Pub. Date: Aug. 6, 2020

(65) Prior Publication Data
US 2022/0089707 A1    Mar. 24, 2022

Related U.S. Application Data

(60) Provisional application No. 62/800,007, filed on Feb. 1, 2019.

(51) Int. Cl.
| | | |
|---|---|---|
| C07K 16/18 | (2006.01) | |
| A61K 39/00 | (2006.01) | |
| A61P 35/00 | (2006.01) | |

(52) U.S. Cl.
CPC .............. *C07K 16/18* (2013.01); *A61P 35/00* (2018.01); *A61K 2039/505* (2013.01); *C07K 2317/32* (2013.01); *C07K 2317/565* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | | |
|---|---|---|---|
| 2010/0129390 A1* | 5/2010 | Yi ........................ | A61P 13/08 435/375 |
| 2012/0023600 A1 | 1/2012 | Shulok et al. | |
| 2015/0231240 A1 | 8/2015 | Chen et al. | |
| 2017/0088625 A1 | 3/2017 | Tedder et al. | |
| 2017/0342137 A1 | 11/2017 | Liao et al. | |

FOREIGN PATENT DOCUMENTS

| | | |
|---|---|---|
| CN | 101600449 A | 12/2009 |
| CN | 107847553 A | 3/2018 |
| CN | 105837690 A | 8/2018 |
| CN | 108463247 A | 8/2018 |
| WO | WO 2018-081437 | 5/2018 |

OTHER PUBLICATIONS

Barker et al. The IPD-IMGT/HLA Database. Nucleic Acids Research (2023) 51 (D1): D948-D955. accessed via the WayBackMachine: https://web.archive.org/web/20180130071221/https://hla.alleles.org/nomenclature/stats.html (Jan. 30, 2018) (Year: 2018).*
Liu and Gao,(2011). Major Histocompatibility Complex: Interaction with Peptides. In eLS, (Ed.). pp. 1-12, https://doi.org/10.1002/9780470015902.a0000922.pub2 (Year: 2011).*
Wieczorek et al. Major Histocompatibility Complex (MHC) Class I and MHC Class II Proteins: Conformational Plasticity in Antigen Presentation. Front. Immunol., Mar. 16, 2017. vol. 8—2017, pp. 1-16 | https://doi.org/10.3389/fimmu.2017.00292 (Year: 2017).*
Wang et al. Human leukocyte antigen (HLA) and cancer immunotherapy: HLA-dependent and -independent adoptive immunotherapies. Ann Blood 2020;5:14 | http://dx.doi.org/10.21037/a (Year: 2020).*
Cary et al. Factors affecting HLA expression: A review. Int J Immunogenet. 2019;46:307-320. DOI: 10.1111/iji.12443 (Year: 2019).*
Hazini et al. Deregulation of HLA-1 in cancer and its central importance for immunotherapy. Journal for ImmunoTherapy of Cancer 2021;9:e002899. doi: 10.1136/jitc-2021-002899 (Year: 2021).*
Zhu et al. Expression and Role of Dickkopf-1 (Dkk1) in tumors: from the cells to the patients. Cancer Management and Research 2021:13, 659-675 (Year: 2021).*
Wei et al. Analyzing the prognostic value of DKK1 expression in human cancers based on bioinformatics. Ann Transl Med 2020;8(8):552 | http://dx.doi.org/10.21037/atm-20-3263 (Year: 2020).*
Trenevska et al. Therapeutic antibodies against intracellular tumor antigens. Front. Immunol. 2017, 8:1001, pp. 1-12, doi: 10.3389/fimmu.2017.01001 (Year: 2017).*
Holstein et al. Update on the role of lenalidomide in patients with multiple myeloma. Ther Adv Hematol 2018, vol. 9(7) 175-190 DOI: 10.1177/ 2040620718775629 (Year: 2018).*
Rosenblatt and Avigan. Targeting the PD/PD-L1 axis in multiple myeloma: a dream or a reality? Blood, Jan. 19, 2017 x vol. 129, No. 3. DOI 10.1182/blood-2016-08- 731885 (Year: 2017).*
Extended European Search Report issued in European Application No. 20748034.4, mailed Oct. 11, 2022.
Glinka et al., "Dickkopf-1 is a Member of a New Family of Secreted Proteins and Functions in Head Induction," Nature, 391:357-362, 1998.

(Continued)

*Primary Examiner* — Amy E Juedes
*Assistant Examiner* — Hilary Ann Petrash
(74) *Attorney, Agent, or Firm* — Parker Highlander PLLC

(57) ABSTRACT

Provided herein are methods and reagents for treating cancer. Methods of treating cancer are provided, comprising administering to a patient in need thereof an effective amount of a DKK1 peptide-loaded MHC antibody provided herein. The methods can further include administering an effective amount of chemotherapy or immunotherapy to said patient.

22 Claims, 22 Drawing Sheets
Specification includes a Sequence Listing.

(56) References Cited

OTHER PUBLICATIONS

Gregory et al., "The Wnt Signaling Inhibitor Dickkopf-1 is Required for Reentry Into the Cell Cycle of Human Adult Stem Cells From Bone Marrow," J. Biol. Chem., 278:28067-28078, 2003.
Klempner et al., "Safety and efficacy of a DKK1 inhibitor . . . ," *Annals of Oncology*, 19(Suppl 8), 2018.
Mao et al., "LDL-Receptor-Related Protein 6 is a Receptor for Dickkopf Proteins," Nature, 411:321-325, 2001.
PCT International Search Report and Written Opinion issued in International Application No. PCT/US2020/016364, mailed Jun. 15, 2020.
Qian et al., "Development of an immunotherapeutic monoclonal antibody recognizing DKK1-HLA-A2 complex to treat human hematologic malignancies," *Blood*, 134(Suppl 1):5551, 2019.
Tian et al., "The Role of the Wnt-Signaling Antagonist DKK1 in the Development of Osteolytic Lesions in Multiple Myeloma," N. Engl. J. Med., 349:2483-2494, 2003.
Yaccoby et al., "Antibody-Based Inhibition of DKK1 Suppresses Tumor-Induced Bone Resorption and Multiple Myeloma Growth In-Vivo," Blood, 109:2106-2111, 2006.
Yamabuki et al., "Dikkopf-1 as a Novel Serologic and Prognostic Biomarker for lung and Esophageal Carcinomas," Cancer Res., 67: 2517-2525, 2007.
Zorn, "Wnt Signaling: Antagonistic Dickkopfs," Curr Biol., 11:R592-595, 2001.
English translation of Office Action issued in Chinese Patent Application No. 202080026280.7, issued Jan. 30, 2024.
Goldstein, S. D. et al., "A monoclonal antibody against the Wnt signaling inhibitor dickkopf-1 inhibits osteosarcoma metastasis in a preclinical model," *Oncotarget*, 7.16 (2016): 21114-21123.

\* cited by examiner

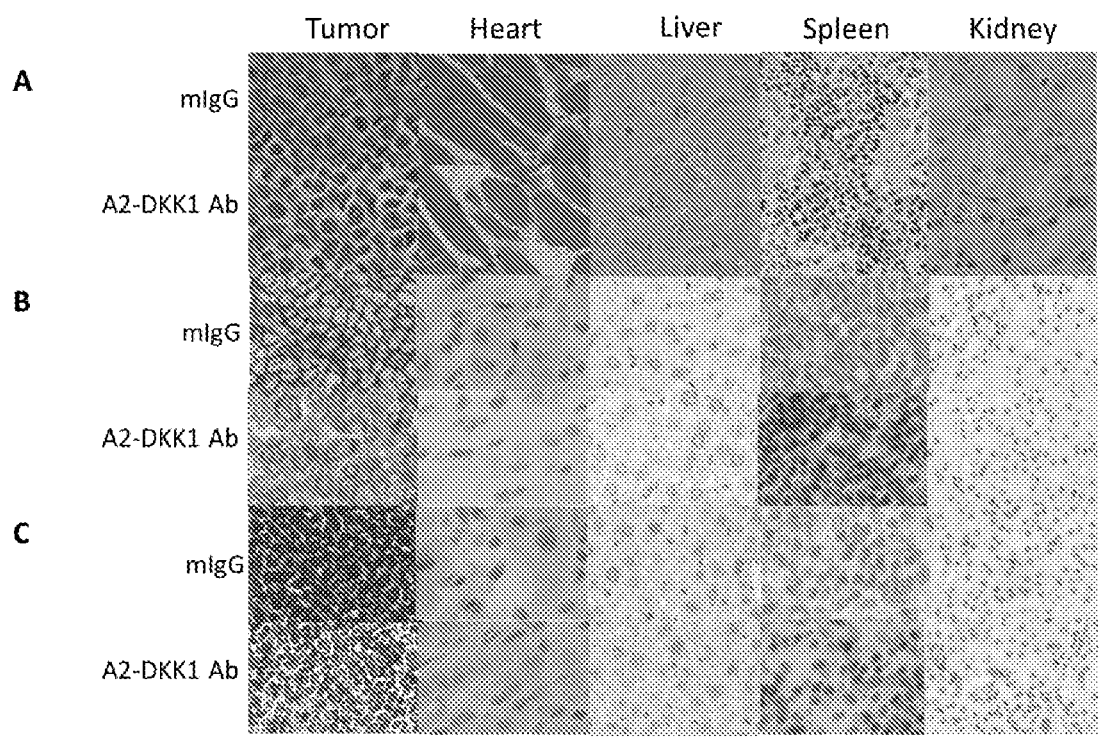
FIGS. 4A-C
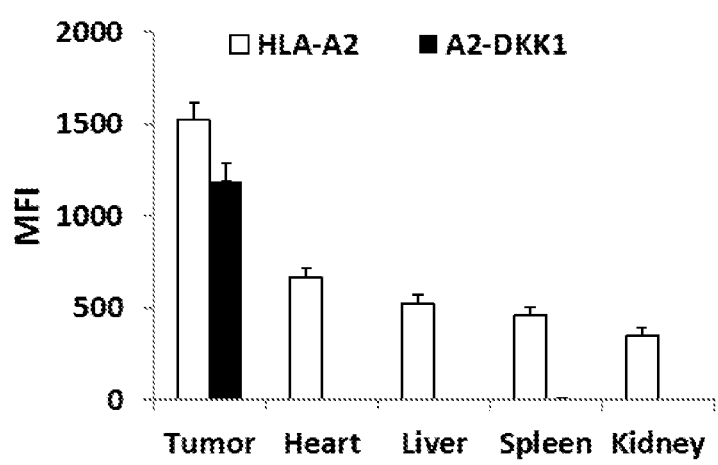
FIG. 4D

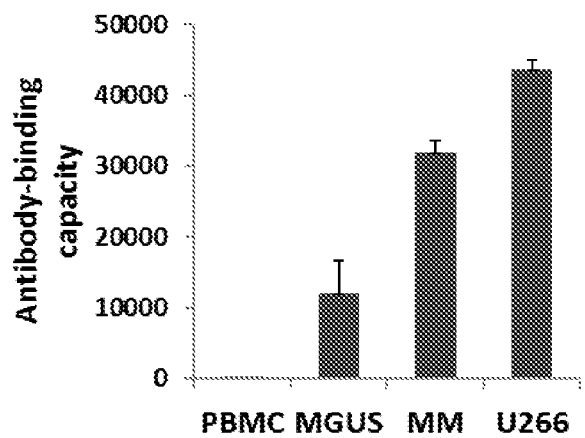
FIG. 7D
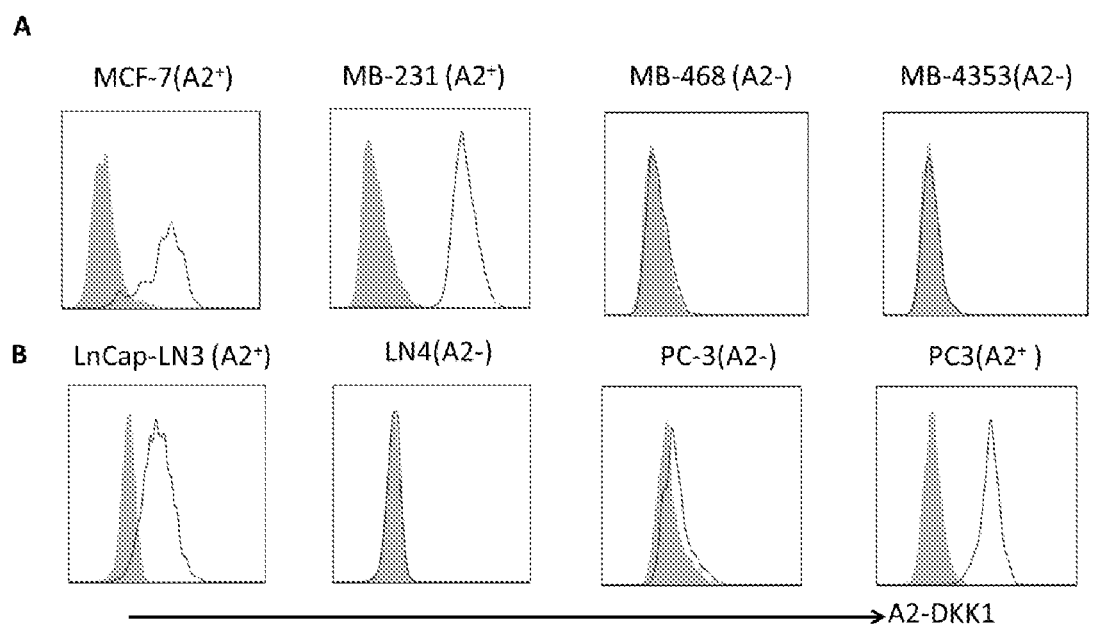
FIGS. 8A-B

SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Ala Leu Gly Gly His Pro Leu Leu Gly Val
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Gly Phe Thr Phe Ser Ser Phe Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Ile Ser Ser Gly Ser Ser Thr Ile
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Ala Arg Pro Tyr Tyr Tyr Gly Ser Thr Tyr Asp Ala Met Asp Tyr
1               5                   10                  15

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Gln Asp Val Gly Ser Thr
1               5

<210> SEQ ID NO 6
<211> LENGTH: 3
<212> TYPE: PRT
<213> ORGANISM: Artificial Sequence
<220> FEATURE:
<223> OTHER INFORMATION: Synthetic peptide

<400> SEQUENCE: 6

Trp Thr Ser
1

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Gln Lys Phe Gly Ser Tyr Pro Leu Thr
1               5

<210> SEQ ID NO 8
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 8

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Tyr Tyr Tyr Gly Ser Thr Tyr Asp Ala Met Asp Tyr Trp
            100                 105                 110

Gly Gln Gly Thr Ser Val Thr Val Ser Ser
        115                 120

<210> SEQ ID NO 9
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 9

Asp Ile Val Met Thr Gln Ser His Lys Leu Met Ser Thr Ser Val Gly
1               5                   10                  15

Asp Arg Val Thr Ile Thr Cys Lys Ala Ser Gln Asp Val Gly Ser Thr
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Val Asp Leu Ala Val Tyr Phe Cys Gln Lys Phe Gly Ser Tyr Pro Leu
                85                  90                  95

Thr Phe Gly Gly Gly Thr Lys Leu Glu Ile Lys
            100                 105

<210> SEQ ID NO 10
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 10

```
gatgtgcagc tggtggagtc tgggggaggc ttagtgcagc ctggagggtc ccggaaactc      60
tcctgtgcag cctctggatt cactttcagt agctttggaa tgcactgggt tcgtcaggct     120
ccagagaagg ggctggagtg ggtcgcatac attagtagtg gcagtagcac catctactat     180
gcagacacag tgaagggccg attcaccatc tccagagaca atcccaagaa caccctgttc     240
ctgcaaatga ccagtctaag gtctgaggac acggccatgt attactgtgc aagaccctat     300
tactacggta gtacctacga tgctatggac tactggggtc aaggaacctc agtcaccgtc     360
tcctca                                                                366
```

<210> SEQ ID NO 11
<211> LENGTH: 322
<212> TYPE: PRT
<213> ORGANISM: Artificial Sequence
<220> FEATURE:
<223> OTHER INFORMATION: Synthetic polynucleotide

<400> SEQUENCE: 11

```
Gly Ala Cys Ala Thr Gly Thr Gly Ala Thr Gly Cys Cys Cys
1               5                   10                  15

Ala Gly Thr Cys Ala Cys Ala Cys Ala Ala Cys Thr Cys Ala Thr
            20                  25                  30

Gly Thr Cys Cys Ala Cys Ala Thr Cys Ala Gly Thr Ala Gly Gly Ala
        35                  40                  45

Gly Ala Cys Ala Gly Gly Gly Thr Cys Ala Cys Cys Ala Thr Cys Ala
            50                  55                  60

Cys Cys Thr Gly Cys Ala Ala Gly Thr Cys Cys Ala Gly Thr Cys Ala
65                  70                  75                  80

Gly Gly Ala Thr Gly Thr Gly Gly Thr Thr Cys Thr Ala Cys Thr
            85                  90                  95

Gly Thr Ala Gly Cys Cys Thr Gly Gly Thr Ala Thr Cys Ala Ala Cys
        100                 105                 110

Ala Gly Ala Ala Ala Cys Cys Ala Gly Gly Thr Cys Ala Ala Thr Cys
            115                 120                 125

Thr Cys Cys Thr Ala Ala Ala Cys Thr Ala Cys Thr Gly Ala Thr Thr
130                 135                 140

Thr Ala Cys Thr Gly Gly Ala Cys Ala Thr Cys Cys Ala Cys Cys
145                 150                 155                 160

Gly Gly Cys Ala Cys Ala Cys Thr Gly Gly Ala Gly Thr Cys Cys Cys
            165                 170                 175

Thr Gly Ala Thr Cys Gly Cys Thr Thr Cys Ala Cys Ala Gly Gly Cys
        180                 185                 190

Ala Gly Thr Gly Gly Ala Thr Cys Thr Gly Gly Ala Cys Ala Gly
            195                 200                 205

Ala Thr Thr Thr Cys Ala Cys Thr Cys Thr Cys Ala Cys Cys Ala Thr
        210                 215                 220

Thr Ala Gly Cys Ala Ala Thr Gly Thr Gly Cys Ala Gly Thr Cys Thr
225                 230                 235                 240
```

-continued

```
Gly Thr Ala Gly Ala Cys Thr Thr Gly Gly Cys Gly Gly Thr Thr Thr
                245                 250                 255

Ala Thr Thr Thr Cys Thr Gly Thr Cys Ala Gly Ala Ala Ala Thr Thr
                260                 265                 270

Thr Gly Gly Cys Ala Gly Thr Thr Ala Thr Cys Cys Thr Cys Thr Gly
        275                 280                 285

Ala Cys Gly Thr Thr Cys Gly Gly Thr Gly Gly Ala Gly Gly Cys Ala
        290                 295                 300

Cys Cys Ala Ala Gly Cys Thr Gly Gly Ala Ala Ala Thr Cys Ala Ala
305                 310                 315                 320

Ala Cys
```

MONOCLONAL ANTIBODIES AGAINST MHC-BOUND HUMAN DICKKOPF-1 PEPTIDES AND USES THEREOF

REFERENCE TO RELATED APPLICATIONS

The present application is a national phase application under 35 U.S.C. § 371 of International Application No. PCT/US2020/016364, filed Feb. 3, 2020, which claims the priority benefit of U.S. provisional application No. 62/800,007, filed Feb. 1, 2019, the entire contents of each of which are incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Jan. 22, 2020, is named UTFCP1418WO_ST25.txt and is 7.4 kilobytes in size.

BACKGROUND

1. Field

The present disclosure relates generally to the fields of medicine, immunology, and cancer biology. More particularly, it concerns antibodies that binding to DKK1 peptide-loaded MHC and methods of their use.

2. Description of Related Art

Studies have shown that Dickkopf-1 (DKK1) is highly expressed by tumor cells of all patients with multiple myeloma but is absent from normal organs or tissues except placenta and prostate. In addition, DKK1 is also expressed by other cancers, such as lymphomas, prostate, lung, and breast cancers. Novartis has a humanized anti-DKK1 mAb (BHQ880) that binds with and neutralizes DKK1. This product is currently under clinical investigation in cancers. However, as DKK1 is a secreted protein, BHQ880 mAb cannot bind with cancer cells and thus may not be therapeutic against the cancer cells. As such, monoclonal antibodies that bind to and kill cancer cells via mediating ADCC and/or CDC are needed.

SUMMARY

Thus, in accordance with the present disclosure, there are provided monoclonal antibodies or antibody fragments, wherein the antibodies or antibody fragments are characterized by clone-paired heavy and light chain CDR sequences from Table 1. The antibody or antibody fragment has heavy chain variable sequence CDRs 1-3 according to SEQ ID NOs: 2, 3, and 4, respectively, and light chain variable sequence CDRs 1-3 according to SEQ ID NOs: 5, 6, and 7, respectively. In various aspects, any given CDR sequence may vary from those of Table 1 by one or two amino acid substitutions. In various aspects, any given CDR sequence may have an at least 70%, 75%, 80%, 85%, 90%, or 95% identity to those of Table 1.

In some aspects, the antibodies or antibody fragments are encoded by light and heavy chain variable sequences according to clone-paired sequences from Table 3. In some aspects, the antibodies or antibody fragments are encoded by light and heavy chain variable sequences having at least 70%, 80%, or 90% identity to clone-paired variable sequences from Table 3. In some aspects, the antibodies or antibody fragments are encoded by light and heavy chain variable sequences having at least 95% identity to clone-paired sequences from Table 3.

In some aspects, the antibodies or antibody fragments are encoded by light and heavy chain variable sequences having at least 70%, 80%, or 90% identity to clone-paired sequences from Table 3. In some aspects, the antibody or antibody fragment is encoded by a heavy chain variable sequence having at least 70%, 80%, or 90% identity to SEQ ID NO: 10 and a light chain variable sequence having at least 70%, 80%, or 90% identity to SEQ ID NO: 11. In some aspects, the antibody or antibody fragment is encoded by a heavy chain variable sequence having at least 95% identity to SEQ ID NO: 10 and a light chain variable sequence having at least 95% identity to SEQ ID NO: 11. In some aspects, the antibody or antibody fragment is encoded by a heavy chain variable sequence according to SEQ ID NO: 10 and a light chain variable sequence according to SEQ ID NO: 11.

In some aspects, the antibodies or antibody fragments comprise light and heavy chain variable sequences according to clone-paired sequences from Table 2. In some aspects, the antibodies or antibody fragments comprise light and heavy chain variable sequences having at least 70%, 80%, or 90% identity to clone-paired variable sequences from Table 2. In some aspects, the antibodies or antibody fragments comprise light and heavy chain variable sequences having 95% identity to clone-paired sequences from Table 2.

In some aspects, the antibody or antibody fragment comprises a heavy chain variable sequence having at least 70%, 80%, or 90% identity to SEQ ID NO: 8 and a light chain variable sequence having at least 70%, 80%, or 90% identity to SEQ ID NO: 9. In some aspects, the antibody or antibody fragment comprises a heavy chain variable sequence having at least 95% identity to SEQ ID NO: 8 and a light chain variable sequence having at least 95% identity to SEQ ID NO: 9. In some aspects, the antibody or antibody fragment comprises a heavy chain variable sequence having a sequence according to SEQ ID NO: 8 and a light chain variable sequence having a sequence according to SEQ ID NO: 9.

Also provided herein are monoclonal antibodies or antigen binding fragments thereof, which compete for binding to the same epitope as any of the monoclonal antibodies or an antigen-binding fragments thereof that are defined herein based on their CDR sequences.

In some aspects, the antibodies or antibody fragments are a humanized antibody. In some aspects, the antibody fragment is a monovalent scFv (single chain fragment variable) antibody, divalent scFv, Fab fragment, F(ab')$_2$ fragment, F(ab')$_3$ fragment, Fv fragment, or single chain antibody. In some aspects, the antibody is a chimeric antibody or bispecific antibody. In some aspects, the antibody is an IgG antibody or a recombinant IgG antibody or antibody fragment. In some aspects, the antibody is conjugated or fused to an imaging agent or a cytotoxic agent.

In one embodiment, provided herein are hybridomas or engineered cells encoding an antibody or antibody fragment of any one of the present embodiments.

In one embodiment, provided herein are methods of treating a patient having a cancer, the method comprising administering an effective amount of a DKK1 peptide-loaded MHC-targeted antibody or antibody fragment. In some aspects, the DKK1 peptide-loaded MHC-targeted antibody or antibody fragment is the antibody or antibody fragment of any one of the present embodiments. In some aspects, the cancer patient has been determined to express an elevated level of DKK1 relative to a control patient.

In some aspects, the methods are further defined as a method for increasing sensitivity to chemotherapy. In some aspects, the methods are further defined as a method for increasing sensitivity to immunotherapy. In some aspects, the cancer is a myeloma, breast cancer, prostate cancer, or lymphoma. In some aspects, the methods are further defined as a method of inhibiting cancer growth.

In some aspects, the methods further comprise administering at least a second anti-cancer therapy. In some aspects, the second anti-cancer therapy is a chemotherapy, immunotherapy, radiotherapy, gene therapy, surgery, hormonal therapy, anti-angiogenic therapy or cytokine therapy. In some aspects, the chemotherapy comprises lenalidomide. In some aspects, the immunotherapy comprises an immune checkpoint inhibitor. In some aspects, the immune checkpoint inhibitor is a CTLA-4 antagonist, a PD-1 antagonist, a PD-L1 antagonist, an OX40 agonist, a LAG3 antagonist, a 4-1BB agonist, or a TIM3 antagonist.

In some aspects, the immune checkpoint inhibitor is a CTLA-4 antagonist. In some aspects, the immune checkpoint inhibitor is a PD1 or PDL1 antagonist. In some aspects, the immune checkpoint inhibitor is a combination of a CTLA-4 antagonist and a PD1 antagonist. In some aspects, the immune checkpoint inhibitor is a combination of a CTLA-4 antagonist and a PDL1 antagonist.

In one embodiment, provided herein are antibodies or antibody fragments of any of the present embodiments for use as a medicament for treating a cancer in a subject. In one embodiment, provided herein are uses of antibodies or antibody fragments of any of the present embodiments in the manufacture of a medicament for the treatment of a cancer.

In one embodiment, provided herein are methods of detecting the presence of cell surface DKK1 peptide/HLA-A2 complexes on cancer cells, the method comprising contacting the cancer cells with a DKK1 peptide-loaded MHC-targeted antibody or antibody fragment. In some aspects, the DKK1 peptide-loaded MHC-targeted antibody or antibody fragment is the antibody or antibody fragment of any one of the present embodiments.

In one embodiment, provided herein are methods of measuring the level of cell surface DKK1 peptide/HLA-A2 complexes on cancer cells, the method comprising contacting the cancer cells with a DKK1 peptide-loaded MHC-targeted antibody or antibody fragment. In some aspects, the DKK1 peptide-loaded MHC-targeted antibody or antibody fragment is the antibody or antibody fragment of any one of the present embodiments.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 4A-E. Toxicity and safety assay of A2-DKK1 mAb in A2-SCID mice. A2-SCID mice were challenged subcutaneously with U266 myeloma cells, followed by treatment with intraperitoneal injections (every three days for a total of six injections) of 400 μg A2-DKK1 mAb (C2) or 400 μg mouse IgG1 (mIgG). Shown are HE staining (FIG. 4A), A2-DKK1 mAb staining (FIG. 4B), Tunel assay (FIGS. 4C and 4E) and mean fluorescent intensity (MFI) (FIG. 4D) of different tissue and tumor from mice receiving different treatment. Representative results of one out of two independent experiments performed are shown. *P<0.05; **P<0.01 (compared with controls).

(FIG. 5A) Peptide binding assay showing specificity of A2-DKK1 mAb (C2), T2 cells were incubated with DKK1 peptides P20 and P66v with different doses overnight and analyzed for surface HLA-A*0201-DKK1 expression (MFI) using A2-DKK1 mAb (C2). (FIG. 5B) T2 cells were incubated with DKK1 peptide P20 with different doses overnight, treated with 100 μg/mL A2-DKK1 mAb (C2) for 48 hours, and analyzed for apoptosis. (FIG. 5C) T2 cells were incubated with DKK1 peptide P20 with different doses overnight, and then analyzed for antibody-binding capacity.

FIGS. 7A-D. Specificity and antibody-binding capacity of A2-DKK1 mAb. (FIG. 7A) Specificity of A2-DKK1 mAb was detected by ELISA coated with different antigens. (FIG. 7B) Peptide binding assay showing specificity of A2-DKK1 mAb, MM cell lines U266 and ARP-1 were incubated with DKK1 peptide P20 overnight, and analyzed for surface HLA-A*0201-DKK1 expression (MFI) by A2-DKK1 mAb. (FIG. 7C) U266 surface binding affinity by A2-DKK1 mAb with different dose. (FIG. 7D) Antibody-binding capacity of A2-DKK1 mAb to normal PBMC, MGUS and MM patient samples, and U266. Error bars=SEM.*p<0.05; **p<0.01.

FIGS. 8A-B. Surface binding to breast and prostate cancer cell lines with A2-DKK1 mAb. Results shown are A2-DKK1 mAb surface binding to breast cancer cell lines (FIG. 8A) and prostate cancer cell lines (FIG. 8B).

(FIGS. 9A and 9B) Apoptosis of U266 induced by A2-DKK1 mAb with different dose. In FIG. 9B, the left column of each pair is "C2" and the right column is "C3". (FIG. 9C) T2 cells were incubated with DKK11 peptide P20 with different dose overnight, then treated with 100 μg/mL A2-DKK1 mAb for 48 hours and analyzed for apoptosis. (FIG. 9D) T2 cell with or without peptide loading. (FIG. 9E) Apoptosis of myeloma and lymphoma cell lines induced by A2-DKK1 mAb. (FIG. 9F) Apoptosis of breast cancer and prostate cancer cell lines induced by A2-DKK1 mAb. Error bars=SEM. *P<0.05; **P<0.01.

(FIG. 10A) Cr-51 release assay detected ADCC of myeloma and lymphoma cell lines induced by A2-DKK1 mAb. In each group of columns, the columns represent, from left to right, U266, ARP-1, Mino, and SP53. (FIG. 10B) Cr-51 release assay detected ADCC of breast and prostate cancer cell lines induced by A2-DKK1 mAb. In each group of columns, the columns represent, from left to right, MCF-7, MDA-MD-231, LNCap-LN3, and PC-3 (A2+). (FIGS. 10C and 10D) IncuCyte ZOOM live imaging system showed ADCC of breast cancer cell line MDA-MB-231 induced by A2-DKK11 mAb. (FIGS. 10E-H) Cr-51 release assay detected ADCC of myeloma (FIG. 10E), lymphoma (FIG. 10E), breast cancer (FIG. 10F), and prostate cancer cell lines (FIG. 10G) as well as T2 cell loaded with different peptides (FIG. 10H) induced by A2-DKK1 mAb, mouse isotype IgG1 and anti-HLA-A2 mAb (BB7.2) as control. Error bars=SEM. *P<0.05; **P<0.01.

(FIG. 11A) Cr-51 release assay detected CDC of myeloma and lymphoma cell lines induced by A2-DKK11 mAb. In each group of columns, the columns represent, from left to right, U266, ARP-1, Mino, and SP53. (FIG. 11B) Cr-51 release assay detected CDC of breast and prostate cancer cell lines induced by A2-DKK1 mAb. In each group of columns, the columns represent, from left to right, MCF-7, MDA-MD-231, LNCap-LN3, and PC-3 (A2+). (FIGS. 11C and D) IncuCyte ZOOM live imaging system showed CDC of breast cancer cell line MDA-MB-231 induced by A2-DKK1 mAb. (FIGS. 11E-G) IncuCyte ZOOM live imaging system detected CDC of prostate cell lines PC-2-A2− (FIG. 11E&G) and PC-2-A2+(FIG. 11F&G) induced by A2-DKK1 mAb, mouse isotype IgG1 as control. Error bars=SEM. *P<0.05; **P<0.01.

DETAILED DESCRIPTION

Figure 1A:
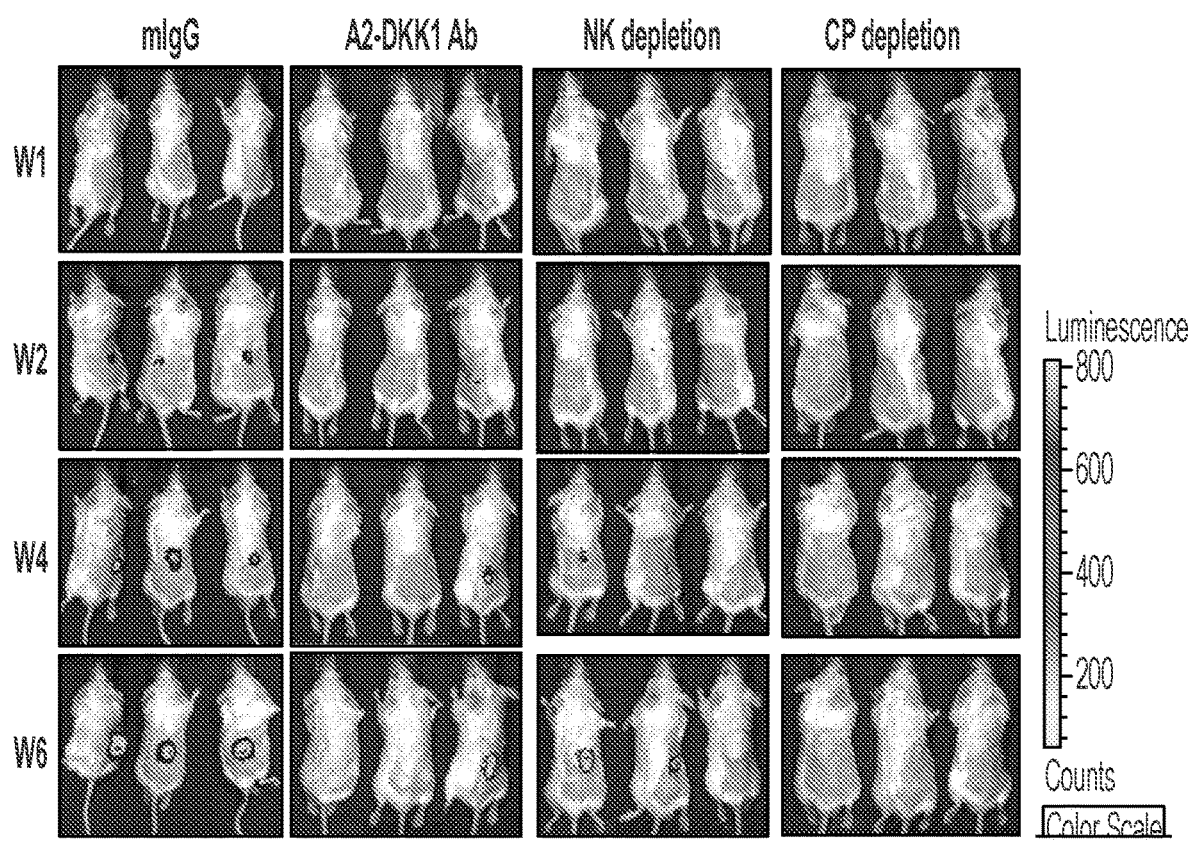
FIGS. 1A-C. Validation of the mechanism of A2-DKK1 mAb action in vivo. Results shown are bioluminescence images (FIG. 1A), tumor burdens (FIG. 1B), and survival (FIG. 1C) of mice receiving different treatments. SCID mice (5 per group) were xenografted subcutaneously with U266 myeloma cells followed by treatment with mouse IgG (mIgG), A2-DKK1 mAb (C2), A2-DKK11 mAb (C2) combined with NK cells depletion by specific mAbs (NK Depletion), and A2-DKK1 mAb (C2) combined with complement depletion by cobra venom factor (CVF) (CP Depletion). Tumor burdens were measured twice every week. Mice were euthanized when subcutaneous tumors reached 225 $mm^2$ or when mice became moribund. Representative results of one out of two independent experiments performed are shown. Error bars=SEM. *$P<0.05$, compared with A2-DKK1 mAb treatment.

DKK11 peptide (such as P20 and P66v, which bind with HLA-A2 molecule)-specific cytotoxic T cells specifically kill myeloma and other cancer cells that express DKK1 and HLA-A2, but not HLA-A2$^+$ normal cells, indicating that DKK1$^+$ tumor cells naturally express these peptides, in the context of HLA-A2 molecules, on their surface. Therefore, DKK11 is a widely expressed, tumor-associated antigen that can be targeted for immunotherapy.

DKK1 peptide P20/HLA-A2 monomer was synthesized and used to immunize mice. Hybridomas secreting monoclonal antibodies (mAbs) recognizing soluble and cell surface-expressing DKK1 P20/HLA-A2 complex were obtained. These mAbs bind specifically with DKK1-expressing, HLA-A2$^+$ cancer cells but not DKK1-expressing, HLA-A2$^-$ cancer cells or DKK1$^-$ HLA-A2$^+$ normal blood cells. Thus, because DKK1 is expressed by cancer cells but not by normal cells, these mAbs have the potential to specifically target cancer cells but not normal cells in HLA-A2$^+$ cancer patients. As most, if not all, therapeutic mAbs kill their target cells via mediating antibody-dependent, cell-mediated cytotoxicity (ADCC) and/or complement-dependent cytotoxicity (CDC), these mAbs may be used to treat patients with myeloma, lymphomas, and solid tumors, such as breast, lung, and prostate, and kill the cancer cells via mediating ADCC and CDC, or delivering toxin to cancer cells. In addition, the murine anti-human DKK1 P20/HLA-A2 mAbs can also be used as a research tool to detect and measure the levels of cell surface DKK1 peptide/HLA-A2 complexes on cancer cells.

I. Dickkopf-1 (DKK1)

Dickkopf-1 (herein also referred to as "DKK1" and sometimes spelled by others as "Dikkopf-1") is a secreted protein that specifically inhibits Wnt/β-catenin signaling by interacting with the co-receptor Lrp-6 (Mao et al., 2001; Zorn, 2001). DKK1 in myeloma patients is associated with the presence of lytic bone lesions (Tian et al., 2003). Immunohistochemical analysis of bone marrow biopsy specimens also showed that only myeloma cells contain detectable DKK1. Recombinant human DKK1 or bone marrow serum containing an elevated level of DKK1 inhibited the differentiation of osteoblast precursor cells in vitro. Furthermore, anti-DKK1 antibody treatment is associated with reduced tumor growth in a myeloma mouse model. As such, DKK1 is an important player in myeloma bone disease and blocking DKK1 activity reduced osteolytic bone resorption, increased bone formation, and helped control myeloma progression (Yaccoby et al., 2006). The DKK11 gene has a restricted expression in placenta and mesenchymal stem cells (MSCs) only and not in other normal tissues (Glinka et al., 1998; Gregory et al., 2003). Furthermore, a gene expression profile analysis of lung and esophageal carcinomas revealed that DKK11 is highly transactivated in the great majority of lung cancers and esophageal squamous cell carcinomas (ESCC) (Yamabuki et al, 2007).

II. Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv, single chain (ScFv)), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. For example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "constant region" of an antibody refers to the constant region of the antibody light chain or the constant region of the antibody heavy chain, either alone or in combination. The constant regions of the light chain (CL) and the heavy chain (CH1, CH2 or CH3, or CH4 in the case of IgM and IgE) confer important biological properties such as secretion, transplacental mobility, Fc receptor binding, complement binding, and the like. By convention the numbering of the constant region domains increases as they become more distal from the antigen binding site or amino-terminus of the antibody.

A "variable region" of an antibody refers to the variable region of the antibody light chain or the variable region of the antibody heavy chain, either alone or in combination. The variable regions of both the light (VL) and heavy (VH) chain portions determine antigen recognition and specificity. VL and VH each consist of four framework regions (FR) connected by three complementarity determining regions (CDRs) also known as hypervariable regions. The CDRs complement an antigen's shape and determine the antibody's affinity and specificity for the antigen. There are six CDRs in both VL and VH. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (the Kabat numbering scheme; see Kabat et al., Sequences of Proteins of Immunological Interest (5th ed., 1991, National Institutes of Health, Bethesda Md.)); and (2) an approach based on crystallographic studies of antigen-antibody complexes (the Chothia numbering scheme which corrects the sites of insertions and deletions (indels) in CDR-L1 and CDR-H1 suggested by Kabat; see Al-lazikani et al. (1997) J. Molec. Biol. 273:927-948)). Other numbering approaches or schemes can also be used. As used herein, a CDR may refer to CDRs defined by either approach or by a combination of both approaches or by other desirable approaches. In addition, a new definition of highly conserved core, boundary and hyper-variable regions can be used.

The term "heavy chain" as used herein refers to the larger immunoglobulin subunit which associates, through its amino terminal region, with the immunoglobulin light chain.

The heavy chain comprises a variable region (VH) and a constant region (CH). The constant region further comprises the CH1, hinge, CH2, and CH3 domains. In the case of IgE, IgM, and IgY, the heavy chain comprises a CH4 domain but does not have a hinge domain. Those skilled in the art will appreciate that heavy chains are classified as gamma, mu, alpha, delta, or epsilon (γ, μ, α, δ, ε), with some subclasses among them (e.g., γ1-γ4). It is the nature of this chain that determines the "class" of the antibody as IgG, IgM, IgA IgG, or IgE, respectively. The immunoglobulin subclasses (isotypes), e.g., IgG1, IgG2, IgG3, IgG4, IgA1, etc. are well characterized and are known to confer functional specialization.

The term "light chain" as used herein refers to the smaller immunoglobulin subunit which associates with the amino terminal region of a heavy chain. As with a heavy chain, a light chain comprises a variable region (VL) and a constant region (CL). Light chains are classified as either kappa or lambda (κ, λ). A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

"Nucleic acid," "nucleic acid sequence," "oligonucleotide," "polynucleotide" or other grammatical equivalents as used herein means at least two nucleotides, either deoxyribonucleotides or ribonucleotides, or analogs thereof, covalently linked together. Polynucleotides are polymers of any length, including, e.g., 20, 50, 100, 200, 300, 500, 1000, 2000, 3000, 5000, 7000, 10,000, etc. A polynucleotide described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. The following are non-limiting examples of polynucleotides: a gene or gene fragment, exons, introns, messenger RNA (mRNA), transfer RNA, ribosomal RNA, ribozymes, cDNA, cRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule. Unless otherwise indicated, a particular polynucleotide sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The terms "peptide," "polypeptide" and "protein" used herein refer to polymers of amino acid residues. These terms also apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers. In the present case, the term "polypeptide" encompasses an antibody or a fragment thereof.

Other terms used in the fields of recombinant nucleic acid technology, microbiology, immunology, antibody engineering, and molecular and cell biology as used herein will be generally understood by one of ordinary skill in the applicable arts.

III. Antibodies and Modifications of Antibodies

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557, incorporated herein by reference). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753, 407; 6,814,965; 6,849,259; 6,861,572; 6,875,434; and 6,891,024, each incorporated herein by reference.

In certain embodiments, are antibody conjugates. The conjugate can be, for example, a specific binding agent (such as an antibody) of the invention conjugated to other proteinaceous, carbohydrate, lipid, or mixed moiety molecule(s). Such antibody conjugates include, but are not limited to, modifications that include linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

In further embodiments, the conjugate can be, for example, a cytotoxic agent. Cytotoxic agents of this type may improve antibody-mediated cytotoxicity, and include such moieties as cytokines that directly or indirectly stimulate cell death, radioisotopes, chemotherapeutic drugs (including prodrugs), bacterial toxins (e.g., *Pseudomonas* exotoxin, diphtheria toxin, etc.), plant toxins (e.g., ricin, gelonin, etc.), chemical conjugates (e.g., maytansinoid toxins, calechaemicin, etc.), radioconjugates, enzyme conjugates (e.g., RNase conjugates, granzyme antibody-directed enzyme/prodrug therapy), and the like. Protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

In additional embodiments, antibodies, or fragments thereof, can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345 and 4,277,437, each incorporated herein by reference. Other labels that will be useful include but are not limited to radioactive labels, fluorescent labels and chemiluminescent labels. U.S. Patents concerning use of such labels include for example U.S. Pat. Nos. 3,817,837; 3,850,752; 3,939,350 and 3,996,345. Any of the peptides of the present invention may comprise one, two, or more of any of these labels.

A. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The monoclonal antibodies may also be isolated from phage antibody libraries using the techniques described in Clackson et al., Nature, 352:624-628 (1991) and Marks et al., J. Mol. Biol., 222:581-597 (1991), for example.

B. Humanized Antibodies and Production Thereof

Where the antibodies or their fragments are intended for therapeutic purposes, it may be desirable to "humanize" them in order to attenuate any immune reaction. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al., J. Steroid Biochem., 26(1):83-92, 1987; Wood et al., J. Clin. Lab. Immunol., 17(4):167-171, 1985; and Shaw et al., J. Natl. Cancer Inst., 80(19):1553-1559, 1988; all of which references are incorporated herein by reference. "Humanized" antibodies can alternatively be produced by CDR or CEA substitution. Jones et al., Nature, 321:522-525, 1986 and Beidler et al., J. Immunol., 141(11): 4053-4060, 1988, each of which is incorporated herein by reference. For this, human $V_H$ and $V_L$ sequences homologous to the $V_H$ and $V_L$ frameworks of the mouse monoclonal antibody can be identified by searching within the GenBank database. The human sequences with the highest homology are then was chosen as an acceptor for humanization. The CDR sequences of mouse monoclonal are then transferred to the corresponding positions of selected human frameworks.

C. General Methods

It will be understood that monoclonal antibodies of the present invention have several applications. These include the production of diagnostic kits for use in detecting DKK11 peptide-loaded MHC, as well as for treating diseases associated with increased levels of DKK1. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce antigen-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

Methods for generating hybrids of antibody-producing cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1 \times 10^{-6}$ to $1 \times 10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

In another aspect, there are provided monoclonal antibodies having clone-paired CDRs from the heavy and light chains as illustrated in Table 1. Such antibodies may be produced using methods described herein.

In another aspect, the antibodies may be defined by their variable sequence, which include additional "framework" regions. These are provided in Tables 2 and 3 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 3 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "Lack Of Fucose On Human IgG N-Linked Oligosaccharide Improves Binding To Human Fcgamma RIII And Antibody-Dependent Cellular Toxicity," J. Biol. Chem. 277(30): 26733-26740; Davies J. et al. (2001) "Expression Of GnTIII In A Recombinant Anti-CD20 CHO Production Cell Line: Expression Of Antibodies With Altered Glycoforms Leads To An Increase In ADCC Through Higher Affinity For FC Gamma RIII," Biotechnology & Bioengineering 74(4): 288-294). Methods of altering carbohydrate contents are known to those skilled in the art, see, e.g., Wallick, S. C. et al. (1988) "Glycosylation Of A VH Residue Of A Monoclonal Antibody Against Alpha (1-6) Dextran Increases Its Affinity For Antigen," J. Exp. Med. 168(3): 1099-1109; Tao, M. H. et al. (1989) "Studies Of Aglycosylated Chimeric Mouse-Human IgG. Role Of Carbohydrate In The Structure And Effector Functions Mediated By The Human IgG Constant Region," *J. Immunol.* 143(8): 2595-2601; Routledge, E. G. et al. (1995) "The Effect Of Aglycosylation On The Immunogenicity Of A Humanized Therapeutic CD3 Monoclonal Antibody," Transplantation 60(8):847-53; Elliott, S. et al. (2003) "Enhancement Of Therapeutic Protein In Vivo Activities Through Glycoengineering," Nature Biotechnol. 21:414-21; Shields, R. L. et al. (2002) "Lack Of Fucose On Human IgG N-Linked Oligosaccharide Improves Binding To Human Fcgamma RIII And Antibody-Dependent Cellular Toxicity," J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1m$\Psi$) outperforms several other nucleoside modifications and their combinations in terms of translation capacity. In addition to turning off the immune/eIF2$\alpha$ phosphorylation-dependent inhibition of translation, incorporated N1m$\Psi$nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fe glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS,* 106 (29), 11937-11942, 2009; Voynov et al., *Biocon. Chem.,* 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H^3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Generally, it is thought that autoreactive clones should be eliminated during ontogeny by negative selection; however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

IV. Treatment of Disease

Certain aspects of the present embodiments can be used to prevent or treat a disease or disorder associated with elevated levels of DKK1, such as cancer. "Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that binds to DKK1 peptide-loaded MHC.

The term "subject" as used herein refers to any individual or patient to which the subject methods are performed. Generally, the subject is human, although as will be appreciated by those in the art, the subject may be an animal. Thus, other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Where clinical application of a therapeutic composition containing an antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain embodiments, the compositions and methods of the present embodiments involve an antibody or an antibody fragment against DKK1 peptide-loaded MHC, in combination with a second or additional therapy, such as chemotherapy or immunotherapy. Such therapy can be applied in the treatment of any disease that is associated with elevated DKK1. For example, the disease may be a cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; myeloma; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, a neurodegenerative disease, and/or a genetic disorder).

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine;

vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; PARP inhibitors, such as olaparib, rucaparib, niraparib, talazoparib, BMN673, iniparib, CEP 9722, or ABT888 (veliparab); CDK4/6 inhibitors, such as ribociclib, palbociclib, abemaciclib, or trilaciclib; androgen inhibitor and anti-androgens, such as cyproterone acetate, megestrol acetate, chlormadinone acetate, spironolactone, oxendolone, osaterone acetate, flutamide, bicalutamide, nilutamide, topilutamide, enzalutamide, apalutamide, dienogest, drospirenone, medrogestone, nomegestrol acetate, promegestone, trimegeston, ketoconazole, abiraterone acetate, seviteronel, aminoglutethimide, finasteride, dutasteride, episteride, alfatradiol, saw palmetto extract (*Serenoa repens*), medrogestone, and bifluranol; carboplatin, procarbazine, plicomycin, gemcitabien, navelbine, farnesyl-protein transferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, an immunotherapy may be an immunomodulatory agent. Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, *Nat Rev Cancer*, 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP_003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Yet another co-stimulatory molecule that can be targeted in the methods provided herein is 4-1BB, also known as CD137, TNFRSF9, and ILA. The complete protein sequence of human 4-1BB has Genbank accession number NP_001552. In some embodiments, the immunomodulatory agent is an anti-4-1BB antibody (e.g., a human antibody, a humanized antibody, or a chimeric antibody), an antigen binding fragment thereof, an immunoadhesin, a fusion protein, or oligopeptide. Anti-human-4-1BB antibodies (or VH and/or VL domains derived therefrom) suitable for use in the present methods can be generated using methods well known in the art. Alternatively, art recognized anti-4-1BB antibodies can be used. An exemplary anti-4-1BB antibody is PF-05082566 (utomilumab; see, e.g., WO 2012/032433).

Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immunoglobulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCDILG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO©, is an anti-PD-1 antibody described in WO2006/121168. Pembrolizumab, also known as MK-3475, Merck 3475, lambrolizumab, KEYTRUDA*, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675, 206, also known as tremelimumab; formerly ticilimumab); U.S. Pat. No. 6,207,156; Hurwitz et al. (1998) Proc Natl Acad Sci USA, 95(17): 10067-10071; Camacho et al. (2004) J Clin Oncology, 22(145): Abstract No. 2505 (antibody CP-675206); and Mokyr et al. (1998) Cancer Res, 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10DI, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP_002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is T-cell immunoglobulin and mucin-domain containing-3 (TIM3), also known as HAVCR2. The complete protein sequence of human TIM3 has Genbank accession number NP_116171. In some embodiments, the immune checkpoint inhibitor is an anti-TIM3 antibody (e.g., a human antibody, a humanized antibody, or a chimeric antibody), an antigen binding fragment thereof, an immunoadhesin, a fusion protein, or oligopeptide. Anti-human-TIM3 antibodies (or VH and/or VL domains derived therefrom) suitable for use in the present methods can be generated using methods well known in the art. Alternatively, art recognized anti-TIM3 antibodies can be used. Exemplary anti-TIM3 antibodies include LY3321367 (see, e.g., WO 2018/039020), MBG453 (see, e.g., WO 2015/117002) and TSR-022 (see, e.g., WO 2018/085469).

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

In some embodiments, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering (Park, Rosenberg et al. 2011). Isolation and transfer of tumor specific T cells has been shown to be successful in treating melanoma. Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors (Jena, Dotti et al. 2010).

In one embodiment, the present application provides for a combination therapy for the treatment of cancer wherein the combination therapy comprises adoptive T cell therapy and a checkpoint inhibitor. In one aspect, the adoptive T cell therapy comprises autologous and/or allogenic T-cells. In another aspect, the autologous and/or allogenic T-cells are targeted against tumor antigens.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

V. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one DKK1 peptide-loaded MHC antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of Monoclonal Antibodies Against DKK1 P20/HLA-A2 Complexes

To generate mAbs specific for DKK1 P20/HLA-A2 complexes, DKK1 P20 (ALGGHPLLGV; SEQ ID NO: 1) peptide was refolded with recombinant human HLA-A2 and β2-microglobulin. Female 6-week-old Balb/c mice were injected intraperitoneally with a 200 μL-suspension composed of 20 μg of purified P20/HLA-A2 monomer (antigen) mixed with complete Freund adjuvant (Fisher Scientific). The mice were immunized at 3-week intervals for a total of three intraperitoneal injections of the antigen plus adjuvant, followed by an intraperitoneal injection of the antigen alone three days before harvest of splenocytes. Three days before the final boost, serum was tested for polyclonal antibodies for binding to P20/HLA-A2 monomer using ELISA. Once mouse sera showed high titers of antibodies binding to the complex, splenocytes from the mouse were fused with SP2/0 myeloma cells, and positive hybridomas were screened by ELISA. Positive clones were isolated by limiting dilution. After screening with parallel ELISA, selected clones were transferred to 24-well plates and grown in RPMI-1640 containing 4 mM L-glutamine and 10% fetal bovine serum. Mice were purchased from The Jackson Laboratory.

Figure 7A:
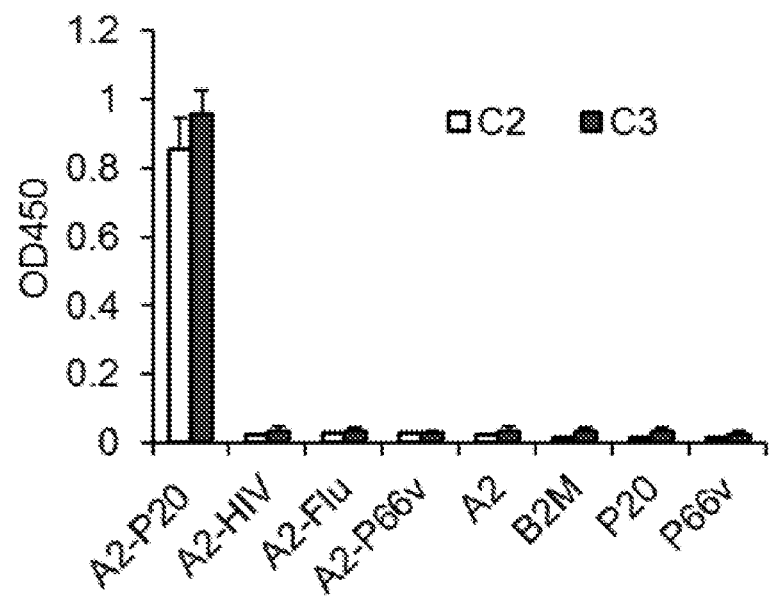
Figure 7B:
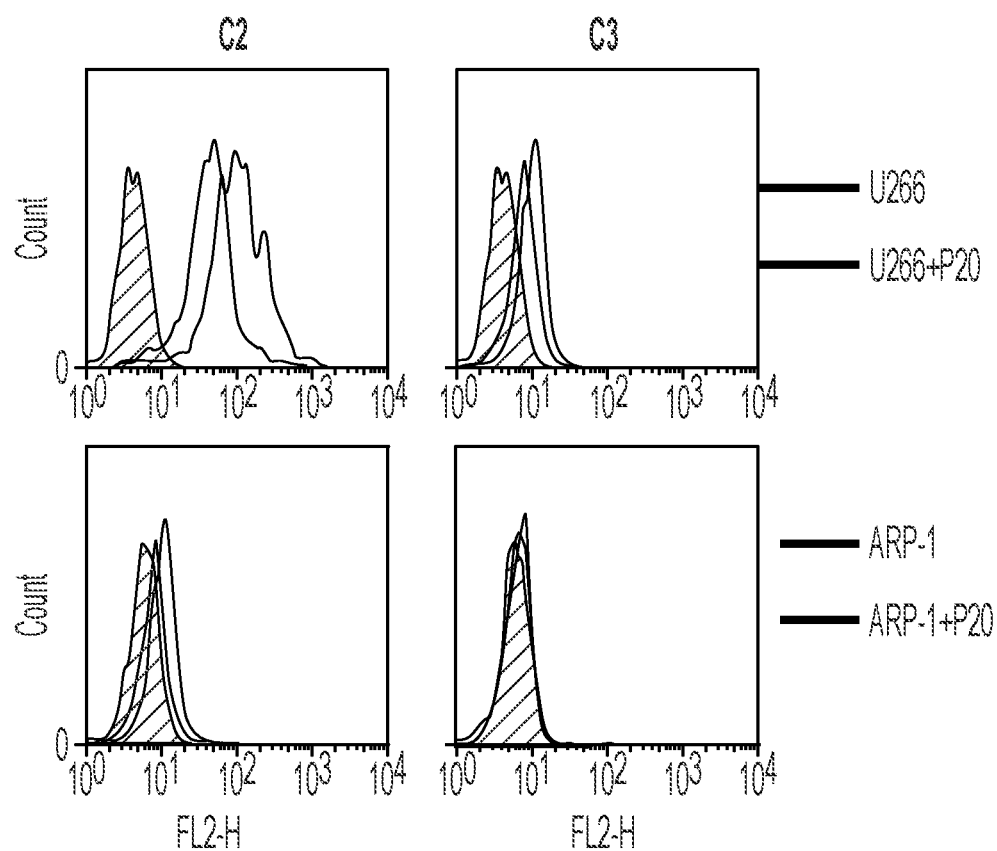

A total of 1920 clones were selected and tested by parallel screening for binding to DKK1 P20/HLA-A2 complex but not to HIV/HLA-A2, an irrelevant HIV control peptide. Two clones (C2 and C3) that showed at least 2-fold higher ELISA signal with P20/HLA-A2 compared with HIV/HLA-A2 were subcloned to generate single-cell-derived colonies. These two clones were confirmed by flow cytometry to bind to U266 myeloma cell line, but not to ARP-1 myeloma cell line, which expresses DKK1 but not HLA-A2 (FIG. 7B). To confirm C2 and C3 specificity, an ELISA was used to show that mAbs from these two clones bound to the P20/HLA-A2 monomer, but not to monomers constructed with other irrelevant peptides that bind tightly to HLA-A2, such as HIV/HLA-A2, Flu/HLA-A2, and cyclin-D1 peptide/HLA-A2 (FIG. 7A). Furthermore, mAbs from C2 and C3 clones did not bind P20 peptide alone, nor to β2-microglobulin. These data show that C2 and C3 mAbs are specific for P20/HLA-A2 complexes. The sequences for C2 are provided in Tables 1-3.

To further confirm that C2 and C3 mAbs bind with P20/HLA-A2 on the cell surface, flow cytometry was used. C2 and C3 mAbs showed specific binding to HLA-A2$^+$ DKK1$^+$ U266 cells, but not to HLA-A2$^-$ DKK1$^+$ ARP cells or DKK1$^-$ HLA-A2$^+$ normal blood cells. Furthermore, the binding to U266 was significantly enhanced after loading U266 cells with P20 peptide (FIG. 7B), further confirming that C2 and C3 mAbs bind specifically with cell-surface P20/HLA-A2 complexes.

TABLE 1

CDRs of heavy chain and light chain variable sequences of antibody C2

| Chain | CDR | Sequence | SEQ ID NO: |
|---|---|---|---|
| Heavy | CDR1 | GFTFSSFG | 2 |
|  | CDR2 | ISSGSSTI | 3 |
|  | CDR3 | ARPYYYGSTYDAMDY | 4 |
| Light | CDR1 | QDVGST | 5 |
|  | CDR2 | WTS | 6 |
|  | CDR3 | QKFGSYPLT | 7 |

TABLE 2

Protein sequences for antibody C2 variable regions

| Chain | Variable Sequence | SEQ ID NO: |
|---|---|---|
| Heavy | DVQLVESGGGLVQPGGSRKLSCAASGFT FSSFGMHWVRQAPEKGLEWVAYISSGSS TIYYADTVKGRFTISRDNPKNTLFLQMT SLRSEDTAMYYCARPYYYGSTYDAMDYW GQGTSVTVSS | 8 |
| Light | DIVMTQSHKLMSTSVGDRVTITCKASQD VGSTVAWYQQKPGQSPKLLIYWTSTRHT GVPDRFTGSGSGTDFTLTISNVQSVDLA VYFCQKFGSYPLTFGGGTKLEIK | 9 |

TABLE 3

Nucleotide sequence of antibody C2 variable regions

| Chain | Variable Sequence (5' to 3') | SEQ ID NO: |
|---|---|---|
| Heavy | GATGTGCAGCTGGTGGAGTCTGGGGGAGG CTTAGTGCAGCCTGGAGGGTCCCGGAAAC TCTCCTGTGCAGCCTCTGGATTCACTTTC AGTAGCTTTGGAATGCACTGGGTTCGTCA GGCTCCAGAGAAGGGGCTGGAGTGGGTCG CATACATTAGTAGTGGCAGTAGCACCATC TACTATGCAGACACAGTGAAGGGCCGATT CACCATCTCCAGAGACAATCCCAAGAACA CCCTGTTCCTGCAAATGACCAGTCTAAGG | 10 |

TABLE 3-continued

Nucleotide sequence of antibody C2 variable regions

| Chain | Variable Sequence (5' to 3') | SEQ ID NO: |
|---|---|---|
|  | TCTGAGGACACGGCCATGTATTACTGTGC AAGACCCTATTACTACGGTAGTACCTACG ATGCTATGGACTACTGGGGTCAAGGAACC TCAGTCACCGTCTCCTCA |  |
| Light | GACATTGTGATGACCCAGTCACACAAACT CATGTCCACATCAGTAGGAGACAGGGTCA CCATCACCTGCAAGGCCAGTCAGGATGTG GGTTCTACTGTAGCCTGGTATCAACAGAA ACCAGGTCAATCTCCTAAACTACTGATTT ACTGGACATCCACCCGGCACACTGGAGTC CCTGATCGCTTCACAGGCAGTGGATCTGG GACAGATTTCACTCTCACCATTAGCAATG TGCAGTCTGTAGACTTGGCGGTTTATTTC TGTCAGAAATTTGGCAGTTATCCTCTGAC GTTCGGTGGAGGCACCAAGCTGGAAATCA AAC | 11 |

Example 2—Monoclonal Antibodies Against DKK1 P20/HLA-A2 Complexes Bind to Cancer Cells that Express DKK1 and HLA-A2

Figure 7C:
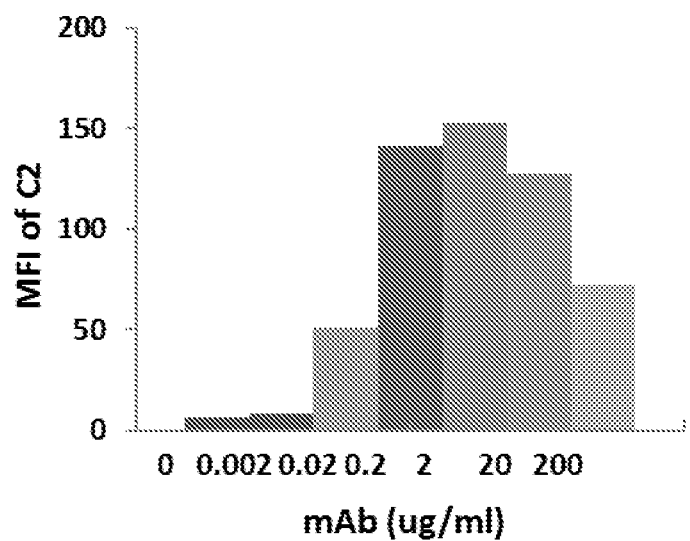

To confirm that DKK1 P20/HLA-A2 is the target molecule of antibody C2, a peptide binding assay was performed using U266 cells and various doses of C2 mAb (FIG. 7C). In addition, peptide binding assays were performed using normal PBMCs as well as monoclonal gammopathy of undetermined significance (MGUS) and (multiple myeloma) MM patient samples (FIG. 7D). The binding of C2 mAb was further tested on breast (FIG. 8A) and prostate (FIG. 8B) cancer cell lines. C2 mAb only bound to the cell lines that were positive for HLA-A2.

Figure 5A:
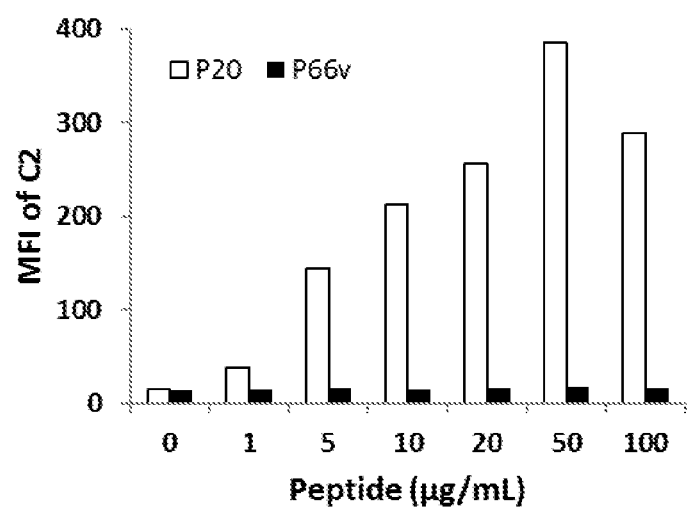
FIGS. 5A-C. Antibody-binding capacity to T2 cell with A2-DKK1 mAb.

Finally, the binding of C2 mAb to T2 cells was studied using peptide binding assays. T2 cells were incubated with DKK1 peptides P20 and P66v with different doses overnight and analyzed for surface HLA-A*0201-DKK1 expression (MFI) using C2 mAb (FIG. 5A). The antibody-binding capacity of T2 cells incubated with different doses of P20 peptide overnight are shown in FIG. 5C.

Figure 5B:
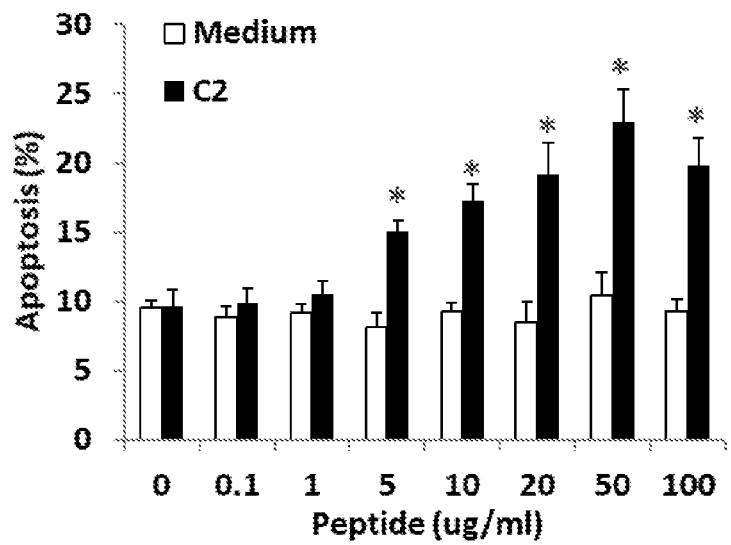
Figure 5C:
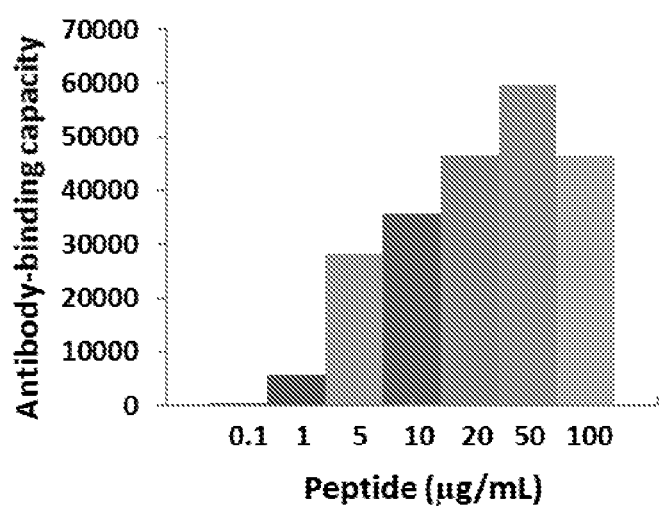
Figure 9A:
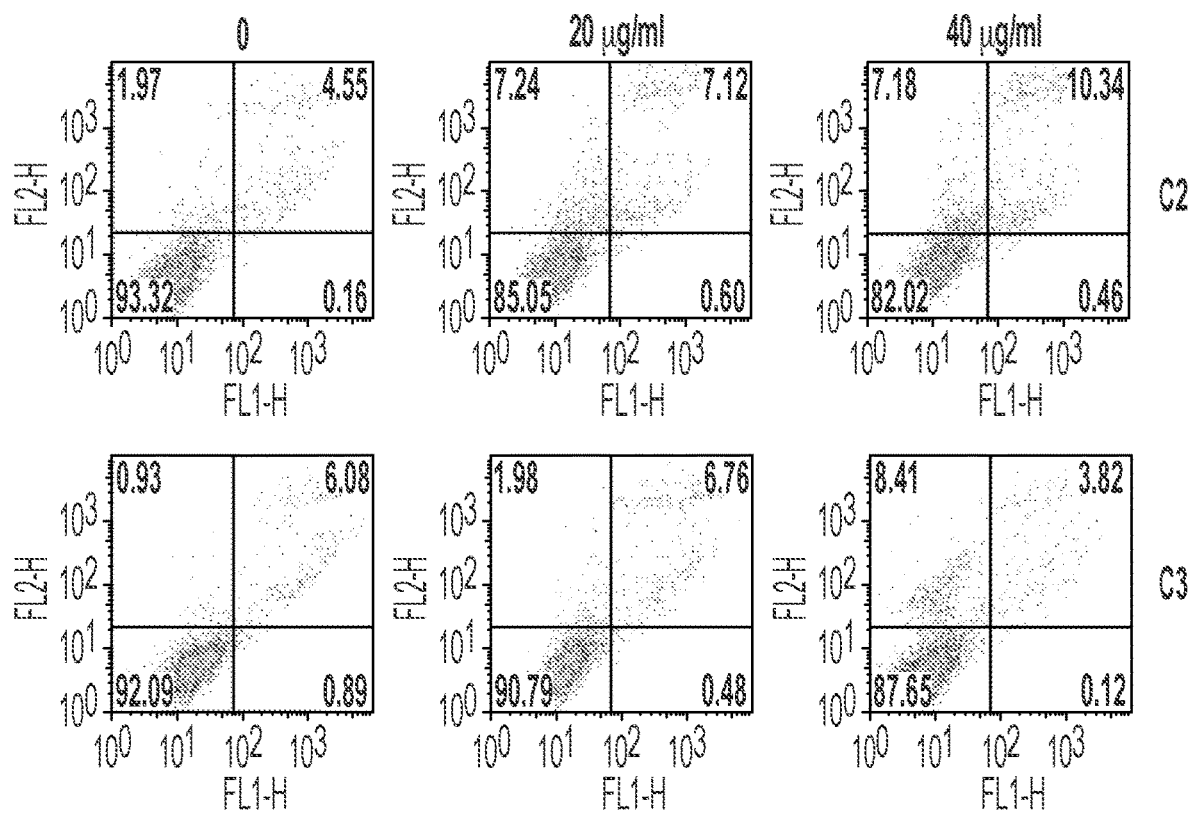
FIGS. 9A-F. Apoptosis of different cancer cells induced by A2-DKK1 mAb in vitro.
Figure 9B:
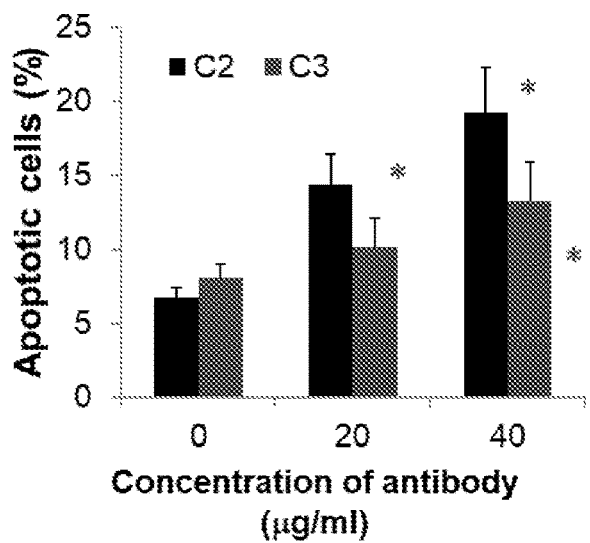
Figure 9C:
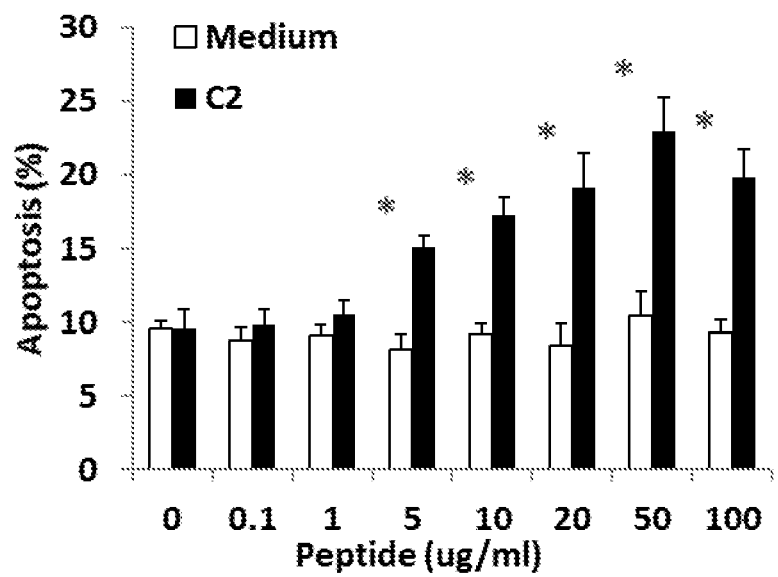
Figure 9D:
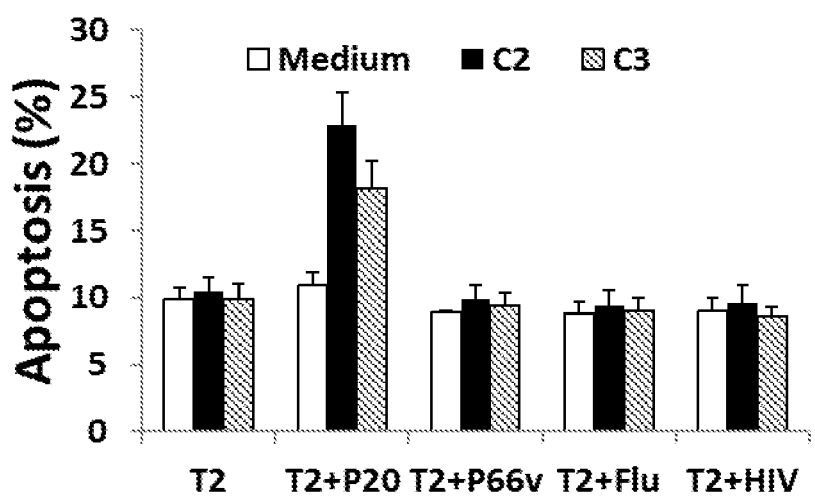
Figure 9E:
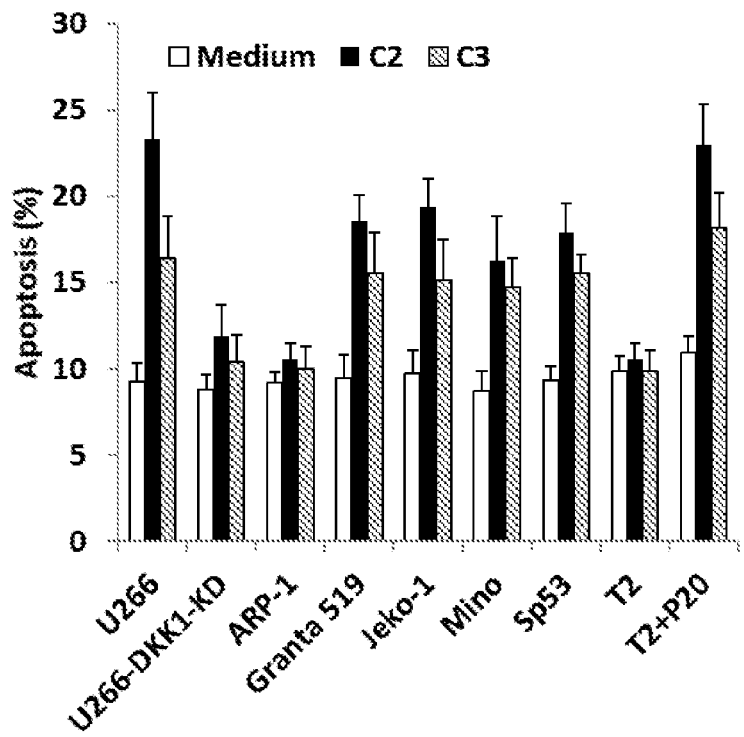
Figure 9F:
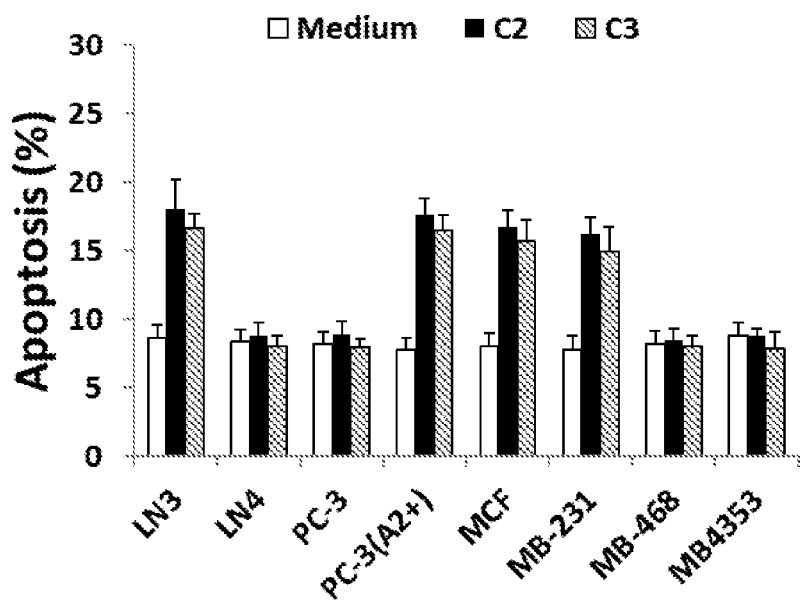

Example 3—In Vitro Function of Monoclonal Antibodies Against DKK1 P20/HLA-A2 Complexes To look at the effect of C2 binding, T2 cells were incubated with DKK11 peptide P20 with different doses overnight, treated with 100 µg/mL A2-DKK1 mAb for 48 hours, and analyzed for apoptosis (FIG. 5B). In addition, U266 cells were incubated with different doses of C2 and C3 mAbs and assayed for apoptosis. Both mAbs induced apoptosis in a dose-dependent manner (FIGS. 9A&B). In addition, T2 cells were incubated with different doses of DKK1 peptide P20 overnight, treated with 100 µg/mL C2 mAb for 48 hours, and analyzed for apoptosis (FIG. 9C). T2 cells were also incubated with either P20 or various non-DKK1 peptides and tested for apoptosis induced by C2 and C3 mAbs. Only the P20-loaded T2 cells underwent increased apoptosis upon binding of C2 and C3 mAbs (FIG. 9D). Finally, the ability of C2 and C3 mAbs to induce apoptosis of myeloma cell lines, lymphoma cell lines (FIG. 9E) and breast cancer and prostate cancer cell lines (FIG. 9F) was also tested.

Figure 10A:
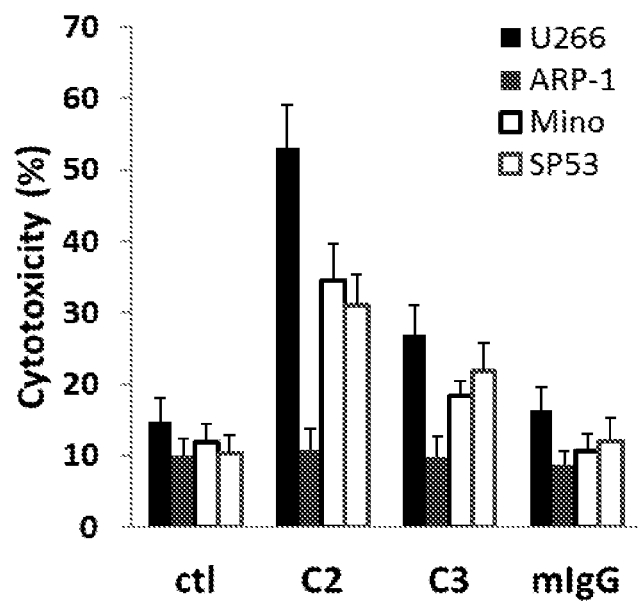
FIGS. 10A-H. ADCC of different cancer cells induced by A2-DKK1 mAb in vitro.
Figure 10B:
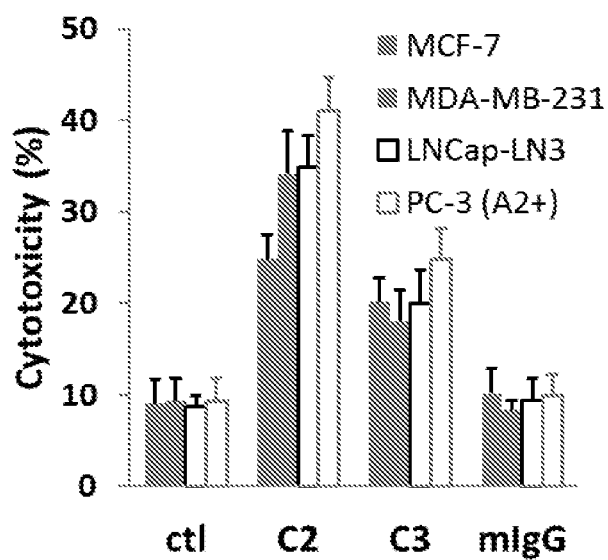
Figure 10C:
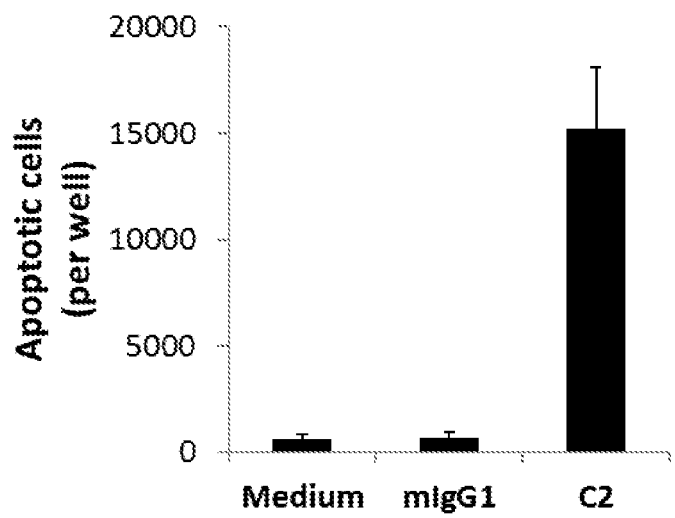
Figure 10D:
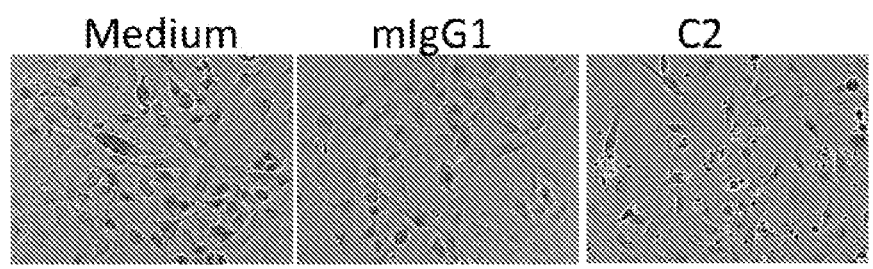
Figure 10E:
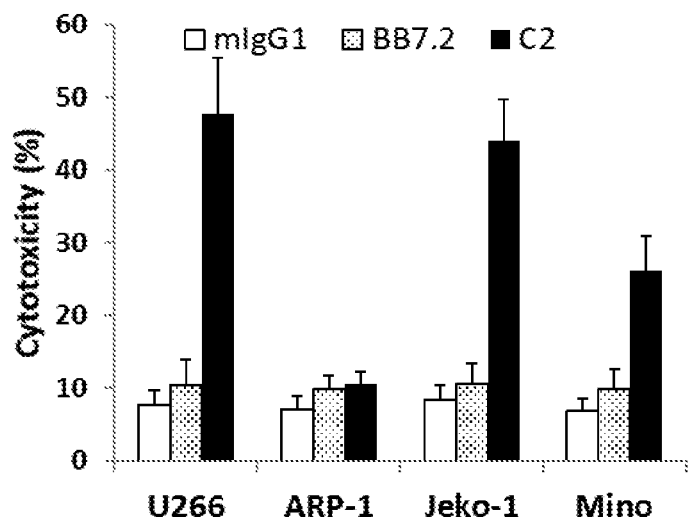
Figure 10F:
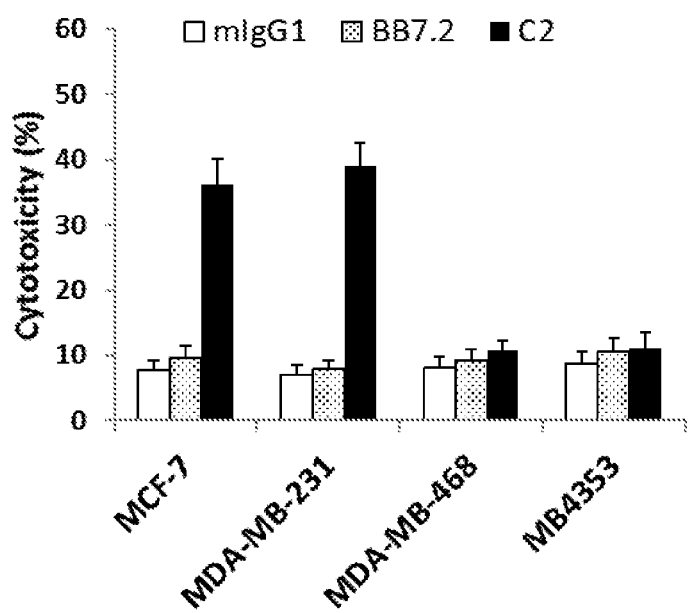
Figure 10G:
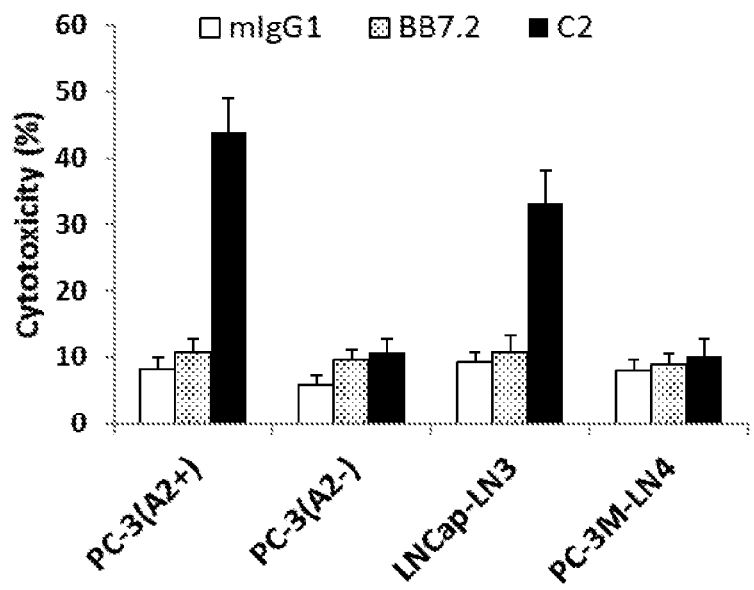
Figure 10H:
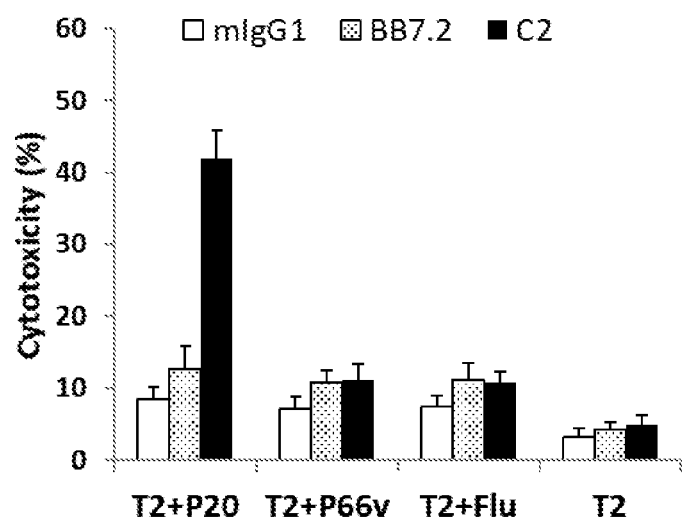

The ability of C2 and C3 mAbs to induce antibody-dependent cellular cytotoxicity was also studied. A Cr-51 release assay detected ADCC of myeloma cell lines (FIGS. 10A&E), lymphoma cell lines (FIGS. 10A&E), breast cancer cell lines (FIGS. 10B&F), and prostate cancer cell lines (FIGS. 10B&G) induced by C2 and C3 mAbs. T2 cells were also incubated with either P20 or various non-DKK1 peptides and tested for ADCC induced by C2 mAbs. Only the P20-loaded T2 cells increased cytotoxicity upon binding of C2 mAb (FIG. 10H). An IncuCyte ZOOM live imaging system showed ADCC of breast cancer cell line MDA-MB-231 induced by C2 mAb (FIGS. 10C&D).

Figure 11A:
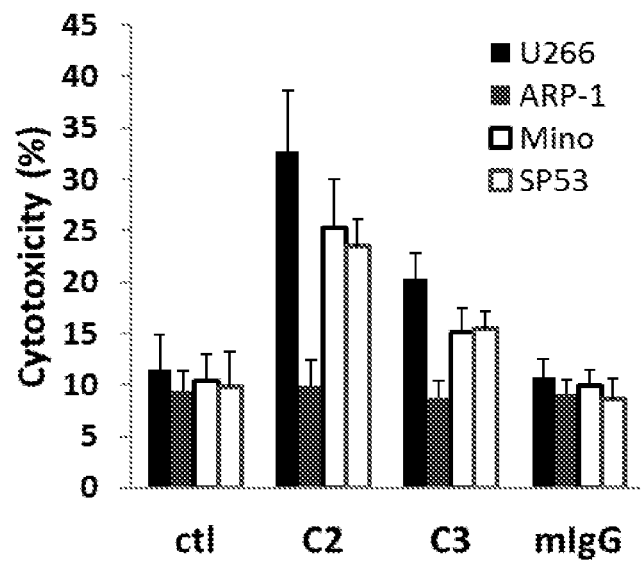
FIGS. 11A-G. CDC of different cancer cells induced by A2-DKK1 mAb in vitro.
Figure 11B:
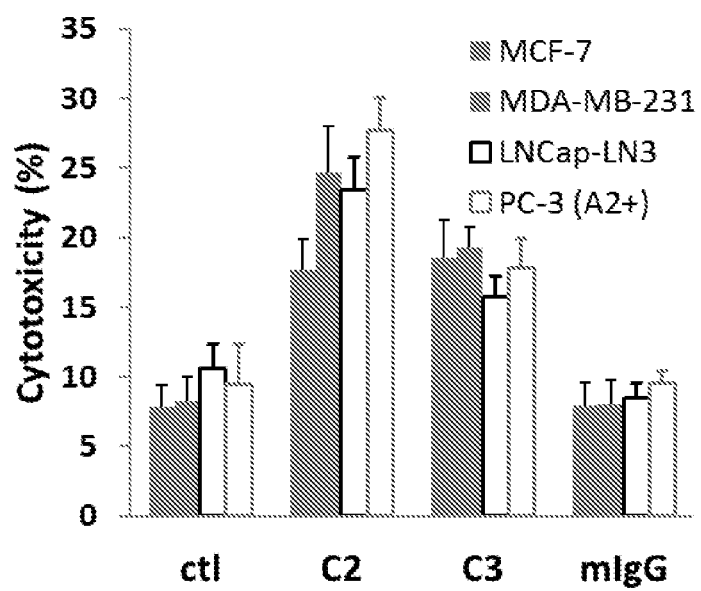
Figure 11C:
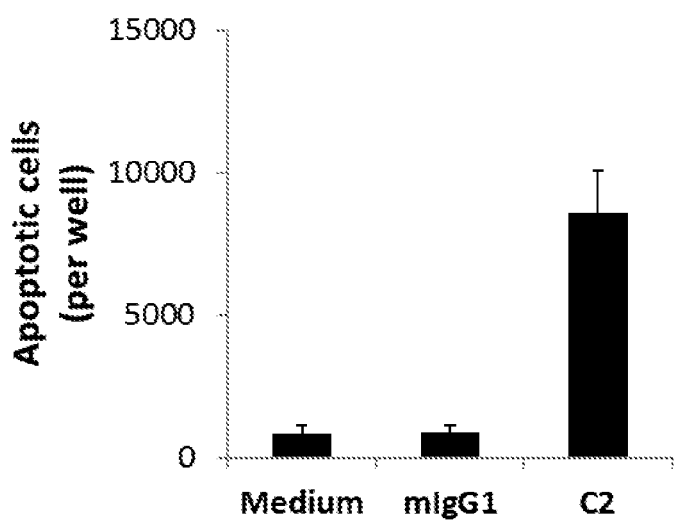
Figure 11D:
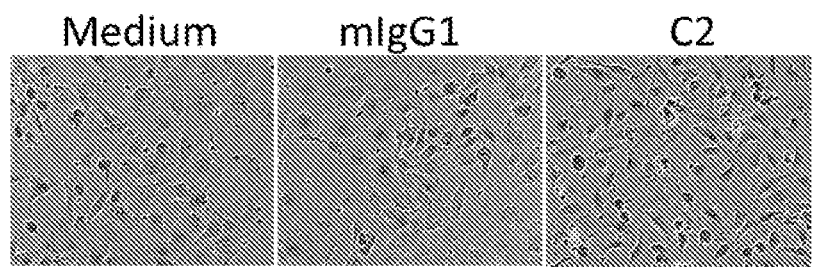
Figure 11E:
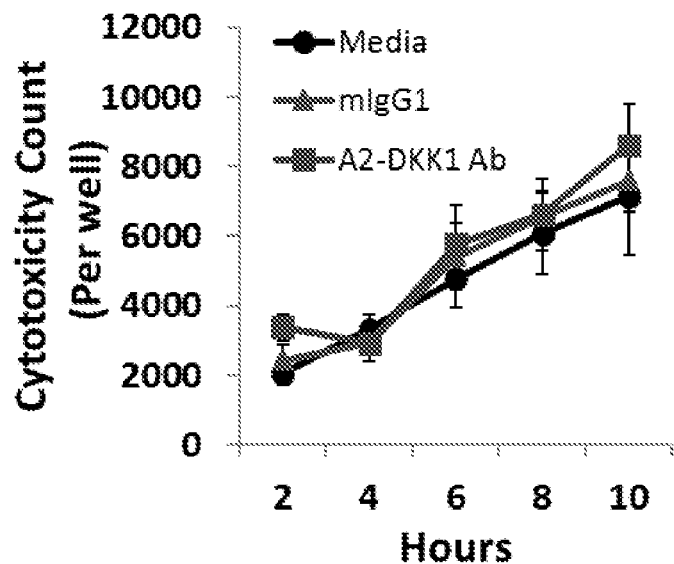
Figure 11F:
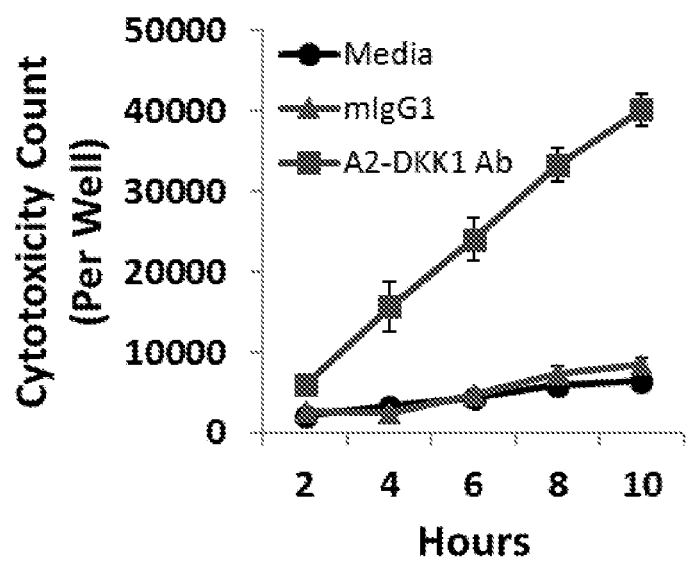
Figure 11G:
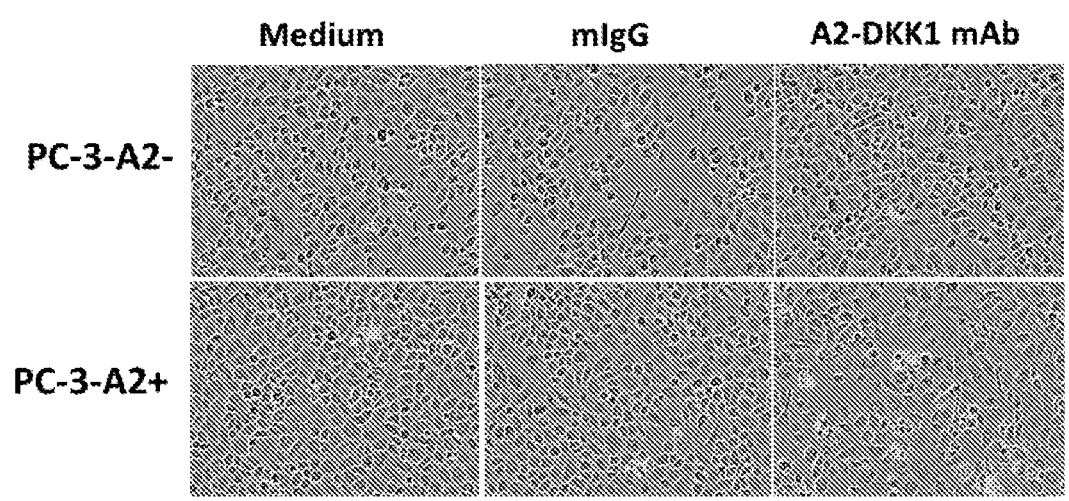

The ability of C2 and C3 mAbs to induce complement-dependent cytotoxicity was tested using different cancer cell lines. A Cr-51 release assay detected CDC of myeloma and lymphoma cell lines (FIG. 11A) as well as breast and prostate cancer cell lines (FIG. 11B) induced by C2 and C3 mAbs. An IncuCyte ZOOM live imaging system showed CDC of breast cancer cell line MDA-MB-231 induced by C2 mAb (FIGS. 11C&D). IncuCyte ZOOM live imaging system also detected CDC of prostate cell lines PC-2-A2− (FIG. 11E&G) and PC-2-A2+(FIG. 11F&G) induced by A2-DKK1 mAb.

Figure 1B:
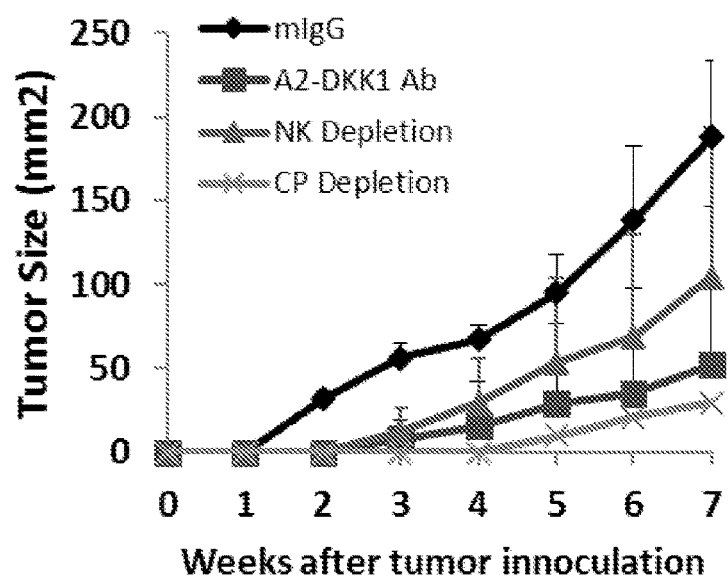
Figure 1C:
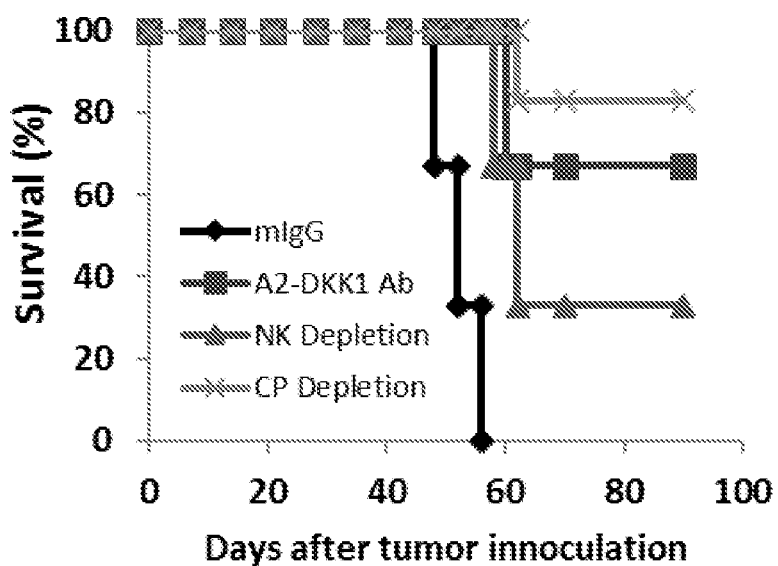

Example 4—In Vivo Function of Monoclonal Antibodies Against DKK1 P20/HLA-A2 Complexes In order to study the mechanism of A2-DKK1 mAbs in vivo, SCID mice (5 per group) were xenografted subcutaneously with U266 myeloma cells followed by treatment with mouse IgG (mIgG), A2-DKK1 mAb, A2-DKK1 mAb combined with NK cells depletion by specific mAbs (NK Depletion), and A2-DKK1 mAb combined with complement depletion by cobra venom factor (CVF) (CP Depletion). Bioluminescence images were obtained at weeks 1, 2, 4, and 6 (FIG. 1A). Tumor burdens were measured twice every week (FIG. 1B). Mice were euthanized when subcutaneous tumors reached 225 mm$^2$ or when mice became moribund. The survival curves are shown in FIG. 1C.

Figure 2A:
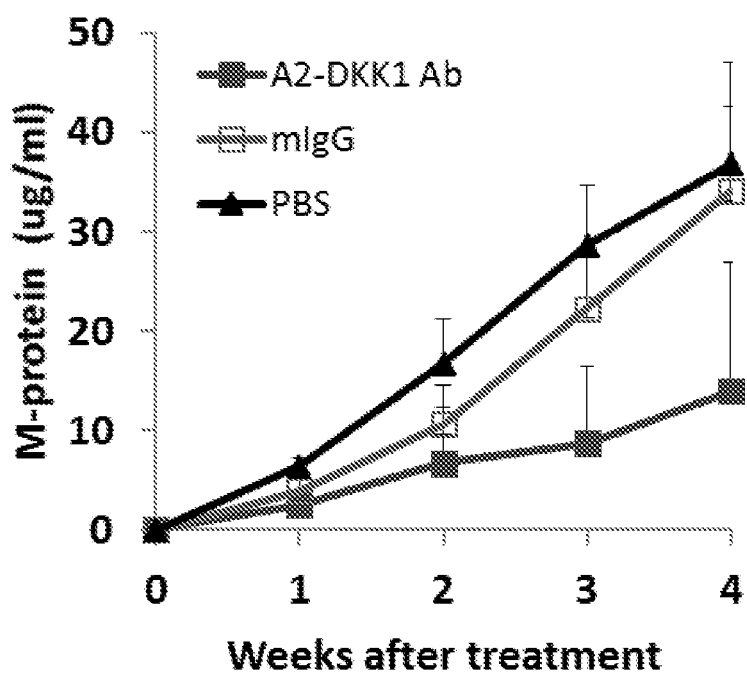
FIGS. 2A-C. Therapeutic benefit in primary MM by A2-DKK1 mAb in SCID-hu model. In SCID-hu mice (six mice per group), primary myeloma cells from HLA-A2 patients (n=3) were directly injected into implanted human bones, and tumor growth was monitored as levels of circulating human M-protein or its light chain. Mice received intraperitoneal injections (every three days for a total of six injections) of 100 μg A2-DKK1 mAb (C2) or 100 μg mouse IgG1, or an equal volume of PBS. Mice were euthanized when circulating human M-protein reached 50 μg/mL or subcutaneous tumors reached 400 $mm^2$. Shown are tumor burdens (FIG. 2A), survival (FIG. 2B), and X-ray images (FIG. 2C) of mice receiving different treatments. Error bars=SEM. *$P<0.05$; **$P<0.01$.
Figure 2B:
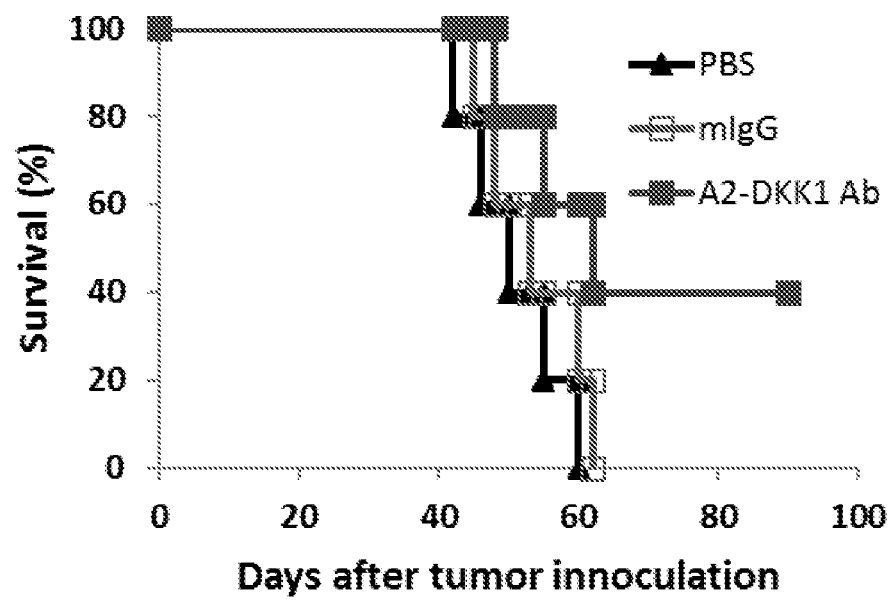
Figure 2C:
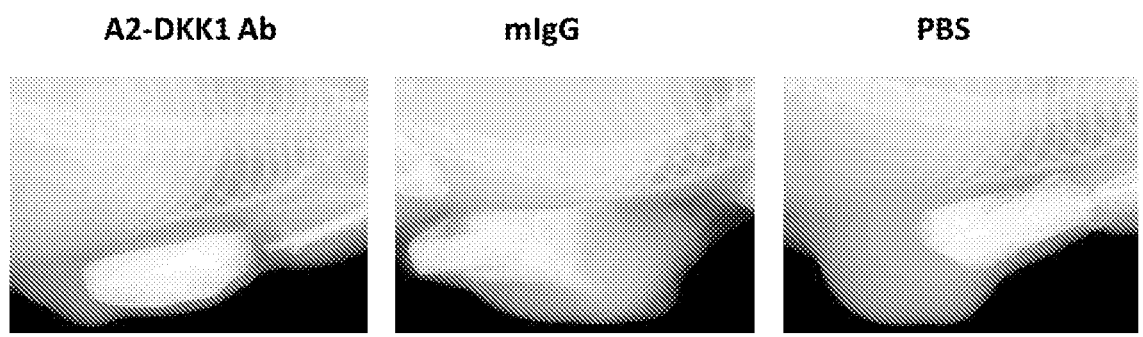

In order to study the therapeutic benefit of A2-DKK1 mAb in primary MM in a SCID-hu model, primary myeloma cells from HLA-A2 patients (n=3) were directly injected into implanted human bones, and tumor growth was monitored as well as levels of circulating human M-protein or its light chain (FIG. 2A). Mice received intraperitoneal injections (every three days for a total of six injections) of 100 μg A2-DKK1 mAb (C2) or 100 μg mouse IgG1, or an equal volume of PBS. Mice were euthanized when circulating human M-protein reached 50 μg/mL or subcutaneous tumors reached 400 mm$^2$. FIG. 2B provides survival curves. FIG. 2C probed X-ray images of mice receiving different treatments.

Figure 3A:
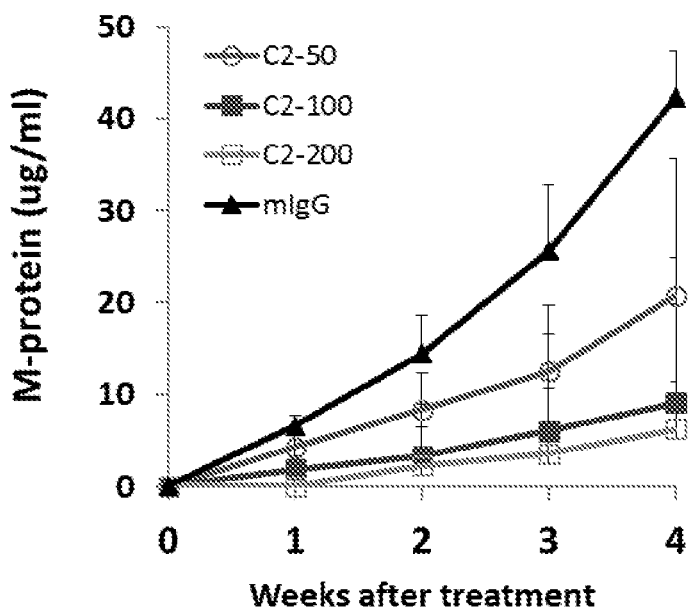
FIGS. 3A-B. Pharmacokinetics of A2-DKK1 mAb in SCID mice. A2-NSG mice were injected intravenously with U266 myeloma cells, followed by treatment with intraperitoneal injections (every three days for a total of six injections) of 50 μg (C2-50), 100 μg (C2-100), 200 μg (C2-200) A2-DKK1 mAb (C2) or 100 μg mouse IgG1. Tumor burdens were monitored as levels of circulating human M-protein or its light chain. Shown are (FIG. 3A) tumor burdens of mice receiving different treatments and (FIG. 3B) pharmacokinetics of A2-DKK1 mAb of mice receiving 100 μg A2-DKK1 mAb treatments. Error bars=SEM. *P<0.05; **P<0.01.
Figure 3B:
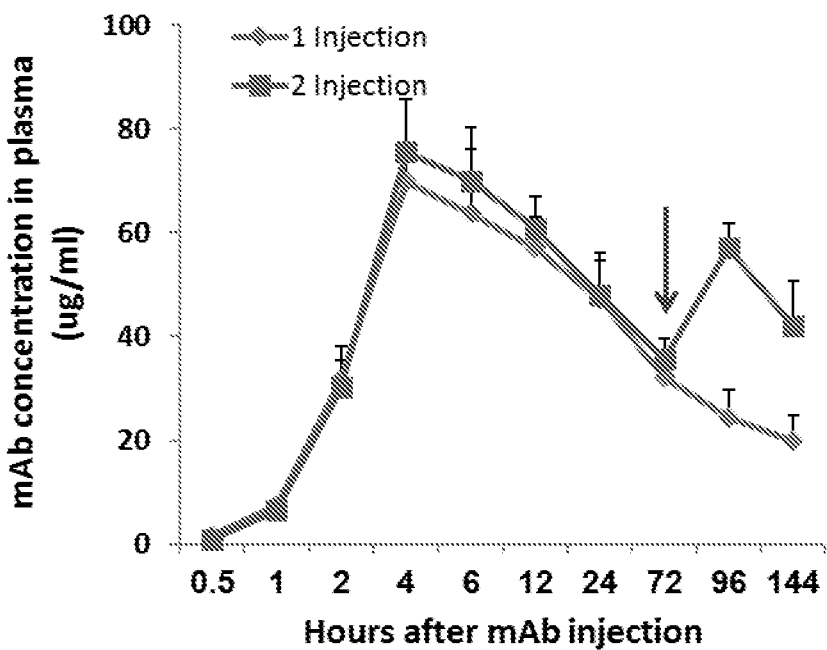

In order to study the pharmacokinetics of A2-DKK1 mAb in SCID mice, A2-NSG mice were injected intravenously with U266 myeloma cells, followed by treatment with intraperitoneal injections (every three days for a total of six injections) of 50 μg (C2-50), 100 μg (C2-100), 200 μg (C2-200) A2-DKK1 mAb or 100 μg mouse IgG1. Tumor burdens were monitored as levels of circulating human M-protein or its light chain (FIG. 3A). The pharmacokinetics of A2-DKK1 mAb of mice receiving 100 μg A2-DKK1 mAb treatments is shown in FIG. 3B.

Figure 4E:
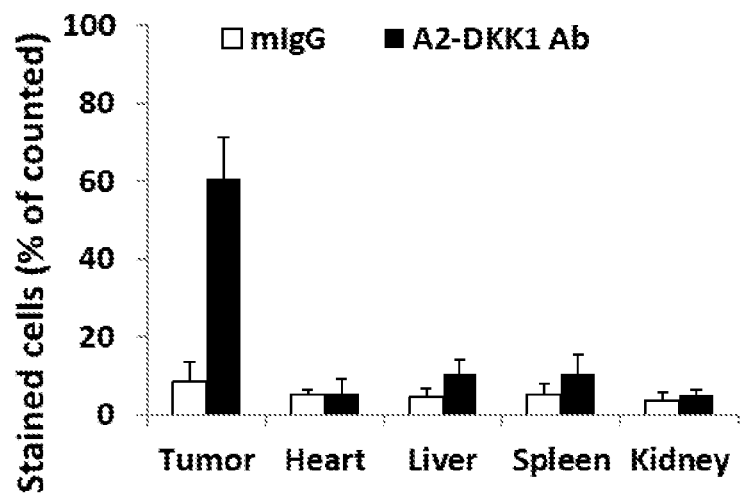

In order to study the toxicity and safety of A2-DKK1 mAb in A2-SCID mice, A2-SCID mice were challenged subcutaneously with U266 myeloma cells, followed by treatment with intraperitoneal injections (every three days for a total of six injections) of 400 μg A2-DKK1 mAb or 400 μg mouse IgG1 (mIgG). Various tissues were analyzed by H&E staining (FIG. 4A), A2-DKK1 mAb staining (FIG. 4B), and Tunel assay (FIGS. 4C&E). FIG. 4D provides the mean fluorescent intensity (MFI) of different tissues and tumor from mice receiving different treatments.

Figure 6A:
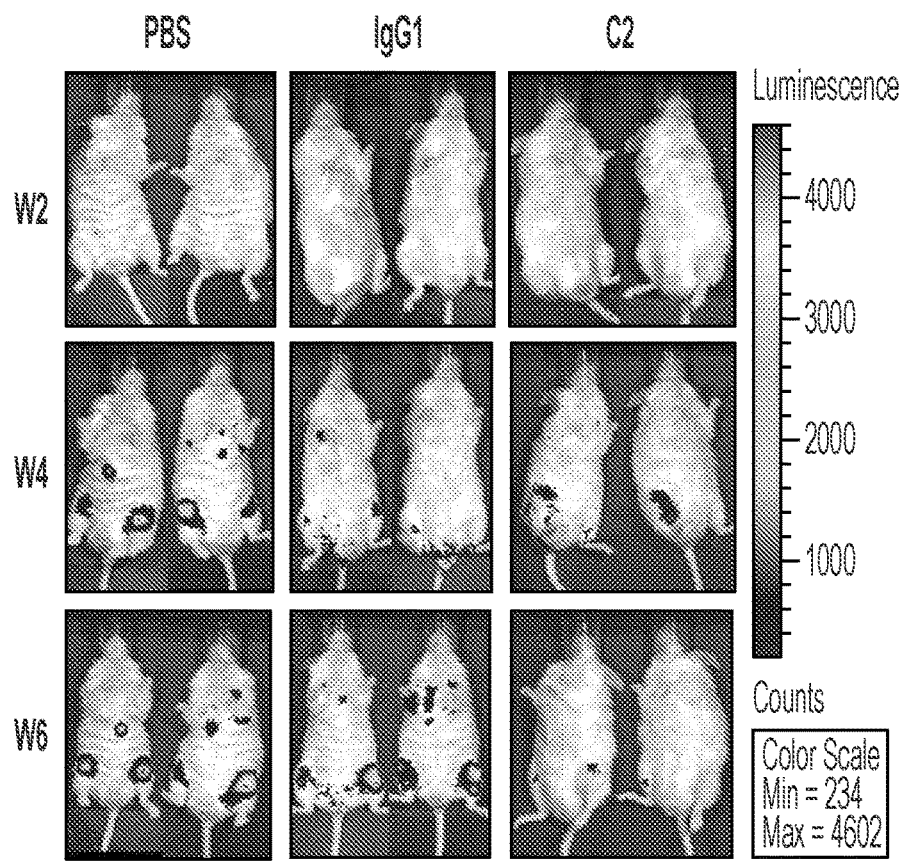
FIGS. 6A-C. Immunotherapy of A2-DKK1 mAb in A2-NSG mouse model. A2-NSG mice were injected intravenously with U266 myeloma cells, followed by treatment with intraperitoneal injections (every three days for a total of six injections) of 100 μg A2-DKK1 mAb (C2) or 100 μg mouse IgG1 (mIgG) or PBS. Tumor burdens were monitored as levels of circulating human M-protein or its light chain. Mice were euthanized when circulating human M-protein reached 50 μg/mL or when mice became moribund. Shown are bioluminescence images (FIG. 6A), tumor burdens (FIG. 6B), and survival (FIG. 6C) of mice receiving different treatments. Error bars=SEM. *P<0.05; **P<0.01.
Figure 6B:
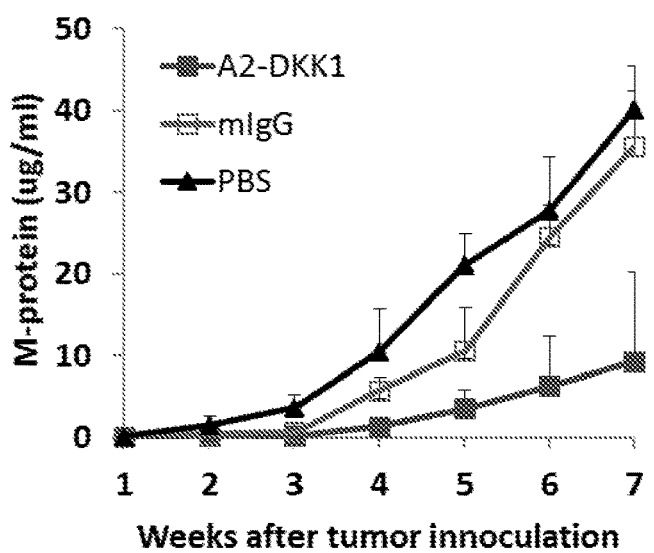
Figure 6C:
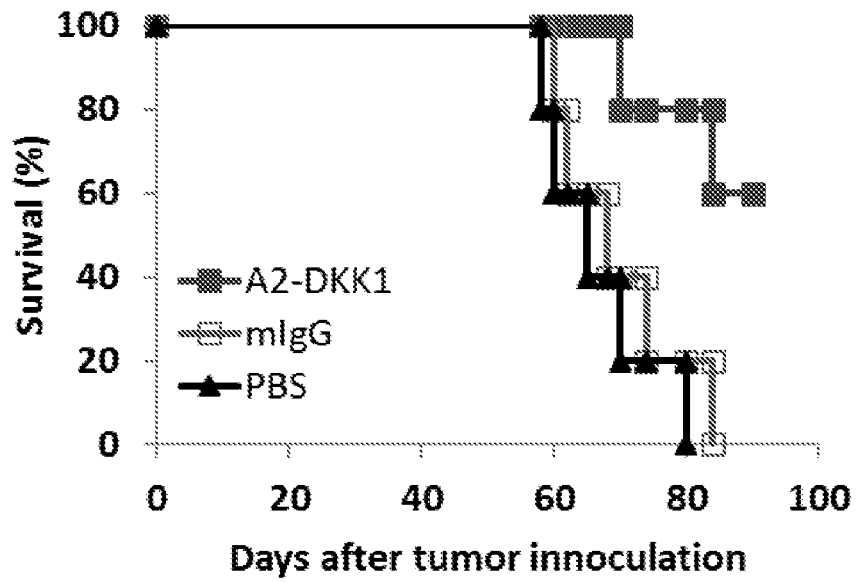

The ability of A2-DKK1 mAb to function as immunotherapy in an A2-NSG mouse model was studied. A2-NSG mice were injected intravenously with U266 myeloma cells, followed by treatment with intraperitoneal injections (every three days for a total of six injections) of 100 μg A2-DKK1 mAb (C2) or 100 μg mouse IgG1 (mIgG) or PBS. Tumor burdens were monitored as levels of circulating human M-protein or its light chain (FIG. 6B). Mice were euthanized when circulating human M-protein reached 50 μg/mL or when mice became moribund. FIG. 6A provides bioluminescence images of mice at weeks 2, 4, and 6. FIG. 6C provides survival curves of mice receiving different treatments.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Glinka et al., "Dickkopf-1 is a Member of a New Family of Secreted Proteins and Functions in Head Induction," *Nature,* 391:357-362, 1998.

Gregory et al., "The Wnt Signaling Inhibitor Dickkopf-1 is Required for Reentry Into the Cell Cycle of Human Adult Stem Cells From Bone Marrow," *J. Biol. Chem.,* 278: 28067-28078, 2003.

Mao et al., "LDL-Receptor-Related Protein 6 is a Receptor for Dickkopf Proteins," *Nature,* 411:321-325, 2001.

Tian et al., "The Role of the Wnt-Signaling Antagonist DKK1 in the Development of Osteolytic Lesions in Multiple Myeloma," *N. Engl. J Med.,* 349:2483-2494, 2003.

Yaccoby et al., "Antibody-Based Inhibition of DKK1 Suppresses Tumor-Induced Bone Resorption and Multiple Myeloma Growth In-Vivo," *Blood,* 109:2106-2111, 2006.

Yamabuki et al., "Dikkopf-1 as a Novel Serologic and Prognostic Biomarker for lung and Esophageal Carcinomas," *Cancer Res.,* 67: 2517-2525, 2007.

Zorn, "Wnt Signaling: Antagonistic Dickkopfs," *Curr Biol.,* 11:R592-595, 2001.

What is claimed is:

1. A monoclonal antibody or antibody fragment, wherein the antibody or antibody fragment comprises:
   a heavy chain variable region (VH) comprising a VHCDR1 amino acid sequence of SEQ ID NO: 2, a VHCDR2 amino acid sequence of SEQ ID NO: 3, and a VHCDR3 amino acid sequence of SEQ ID NO: 4; and
   a light chain variable region (VL) comprising a VLCDR1 amino acid sequence of SEQ ID NO: 5, a VLCDR2 amino acid sequence of SEQ ID NO: 6, and a VLCDR3 amino acid sequence of SEQ ID NO: 7.

2. The monoclonal antibody or antibody fragment of claim 1, wherein said antibody or antibody fragment comprises a heavy chain variable sequence encoded by a first nucleic acid sequence having at least 70%, 80%, or 90% identity to SEQ ID NO: 10 and a light chain variable sequence encoded by a second nucleic acid sequence having at least 70%, 80%, or 90% identity to SEQ ID NO: 11.

3. The monoclonal antibody or antibody fragment of claim 1, wherein said antibody or antibody fragment comprises a heavy chain variable sequence encoded by a first nucleic acid sequence having at least 95% identity to SEQ ID NO: 10 and a light chain variable sequence encoded by a second nucleic acid sequence having at least 95% identity to SEQ ID NO: 11.

4. The monoclonal antibody or antibody fragment of claim 1, wherein said antibody or antibody fragment comprises a heavy chain variable sequence encoded by a first nucleic acid sequence according to SEQ ID NO: 10 and a light chain variable sequence encoded by a first nucleic acid sequence according to SEQ ID NO: 11.

5. The monoclonal antibody or antibody fragment of claim 1, wherein said antibody or antibody fragment comprises a heavy chain variable sequence having at least 70%, 80%, or 90% identity to SEQ ID NO: 8 and a light chain variable sequence having at least 70%, 80%, or 90% identity to SEQ ID NO: 9.

6. The monoclonal antibody or antibody fragment of claim 1, wherein said antibody or antibody fragment comprises a heavy chain variable sequence having at least 95% identity to SEQ ID NO: 8 and a light chain variable sequence having at least 95% identity to SEQ ID NO: 9.

7. The monoclonal antibody or antibody fragment of claim 1, wherein said antibody or antibody fragment comprises a heavy chain variable sequence having a sequence according to SEQ ID NO: 8 and a light chain variable sequence having a sequence according to SEQ ID NO: 9.

8. The monoclonal antibody or antibody fragment of claim 1, wherein said antibody or antibody fragment is a humanized antibody.

9. A hybridoma or engineered cell encoding expressing an antibody or antibody fragment of claim 1.

10. A method of treating a patient having multiple myeloma, lymphoma, prostate, or breast cancer, and wherein the patient is positive for both DKK1 and HLA-A*0201, the method comprising administering an effective amount of an antibody or antibody fragment that targets a DKK1 peptide-loaded MHC, wherein the DKK1 peptide-loaded MHC antibody or antibody fragment comprises: a heavy chain variable region (VH) comprising a VHCDR1 amino acid sequence of SEQ ID NO: 2, a VHCDR2 amino acid sequence of SEQ ID NO: 3, and a VHCDR3 amino acid sequence of SEQ ID NO: 4; and a light chain variable region (VL) comprising a VLCDR1 amino acid sequence of SEQ ID NO: 5, a VLCDR2 amino acid sequence of SEQ ID NO: 6, and a VLCDR3 amino acid sequence of SEQ ID NO: 7.

11. The method of claim 10, wherein said cancer patient has been determined to express an elevated level of DKK1 relative to a control patient.

12. The method of claim 10, wherein the method increases sensitivity to chemotherapy.

13. The method of claim 10, wherein the method increases sensitivity to immunotherapy.

14. The method of claim 10, wherein the method inhibits cancer growth.

15. The method of claim 10, further comprising administering at least a second anti-cancer therapy.

16. The method of claim 15, wherein the second anti-cancer therapy is a chemotherapy, immunotherapy, radiotherapy, gene therapy, surgery, hormonal therapy, anti-angiogenic therapy or cytokine therapy.

17. The method of claim 16, wherein the chemotherapy comprises lenalidomide.

18. The method of claim 16, wherein the immunotherapy comprises an immune checkpoint inhibitor.

19. The method of claim 18, wherein the immune checkpoint inhibitor is a CTLA-4 antagonist, a PD-1 antagonist, a PD-L1 antagonist, an OX40 agonist, a LAG3 antagonist, a 4-1BB agonist, or a TIM3 antagonist.

20. The method of claim 18, wherein the immune checkpoint inhibitor is a combination of a CTLA-4 antagonist and a PD1 antagonist.

21. The method of claim 18, wherein the immune checkpoint inhibitor is a combination of a CTLA-4 antagonist and a PDL1 antagonist.

22. A method of detecting the presence of cell surface DKK1 peptide-loaded HLA-A2*0201 complexes on cancer cells, the method comprising contacting the cancer cells with the antibody or antibody fragment of claim 1.

* * * * *